US012697284B2

(12) United States Patent
Rosenbaum et al.

(10) Patent No.: US 12,697,284 B2
(45) Date of Patent: Aug. 4, 2026

(54) CAPSULE DEVICE WITH AN APERTURE FORMED BY AN OVERLAP OF TWO HALVE-CAPSULE SHELLS

(71) Applicant: EsoCap AG, Basel (CH)

(72) Inventors: Christoph Rosenbaum, Greifswald (DE); Viviane Gamboni, Aarau Rohr (CH); Silvio Moser, Rütihof (CH); Peter Frech, Brüttisellen (CH); Andreas Kaiser, Kaisten (CH); Peter Stangier, Grenzach-Wyhlen (DE)

(73) Assignee: EsoCap AG (CH)

( * ) Notice: Subject to any disclaimer, the term of this patent is extended or adjusted under 35 U.S.C. 154(b) by 364 days.

(21) Appl. No.: 18/561,198

(22) PCT Filed: May 20, 2022

(86) PCT No.: PCT/EP2022/063730
§ 371 (c)(1),
(2) Date: Nov. 15, 2023

(87) PCT Pub. No.: WO2022/243516
PCT Pub. Date: Nov. 24, 2022

(65) Prior Publication Data
US 2024/0226519 A1 Jul. 11, 2024

(30) Foreign Application Priority Data
May 21, 2021 (EP) ..................................... 21175427

(51) Int. Cl.
| | |
|---|---|
| *A61K 31/00* | (2006.01) |
| *A61J 3/07* | (2006.01) |
| *A61J 7/00* | (2006.01) |
| *A61K 9/00* | (2006.01) |
(Continued)

(52) U.S. Cl.
CPC ............... *A61J 3/071* (2013.01); *A61J 3/074* (2013.01); *A61J 3/077* (2013.01); *A61J 7/0061* (2013.01);
(Continued)

(58) Field of Classification Search
CPC .. A61J 3/071; A61J 3/074; A61J 3/077; A61J 7/0061; A61K 9/0046; A61K 9/006;
(Continued)

(56) References Cited

U.S. PATENT DOCUMENTS

| | | |
|---|---|---|
| 3,528,429 A | 9/1970 | Beal et al. |
| 4,076,848 A | 2/1978 | De Limur |
(Continued)

FOREIGN PATENT DOCUMENTS

| | | |
|---|---|---|
| CN | 107249575 A | 10/2017 |
| DE | 102014119576 A1 | 6/2016 |
(Continued)

OTHER PUBLICATIONS

European Search Report dated Nov. 2, 2021 issued in U.S. Appl. No. 21175436.1.
(Continued)

*Primary Examiner* — John Kim
(74) *Attorney, Agent, or Firm* — Dorsey & Whitney LLP

(57) ABSTRACT

The present invention relates to a pharmaceutical dosage form for application to a mucous membrane, in particular to a buccal, intestinal, rectal or vaginal mucous membrane, comprising at least one string-like or strip-like preparation comprising the active pharmaceutical ingredient, the dosage from consisting a first and a second halve-capsule shell, which jointly define the size of an aperture for releasing the preparation. The invention also relates to a method of producing the pharmaceutical dosage form.

20 Claims, 12 Drawing Sheets

(51) Int. Cl.
    *A61K 9/48*         (2006.01)
    *A61M 31/00*      (2006.01)

(52) U.S. Cl.
    CPC ............ *A61K 9/0046* (2013.01); *A61K 9/006* (2013.01); *A61K 9/0065* (2013.01); *A61K 9/4808* (2013.01); *A61K 9/4866* (2013.01); *A61K 31/00* (2013.01); *A61M 31/002* (2013.01); *A61M 2207/00* (2013.01)

(58) Field of Classification Search
    CPC .. A61K 9/0065; A61K 9/4808; A61K 9/4866; A61K 31/00; A61M 31/002; A61M 2207/00
    See application file for complete search history.

(56)           References Cited

U.S. PATENT DOCUMENTS

| | | |
|---|---|---|
| 8,865,209 B1 | 10/2014 | Busiashvili |
| 2015/0011874 A1 | 1/2015 | Amoako-Tuffour et al. |
| 2020/0138416 A1 | 5/2020 | Shalon |

FOREIGN PATENT DOCUMENTS

| | | |
|---|---|---|
| JP | 2003508106 A | 3/2003 |
| JP | 2018501878 A | 1/2018 |
| RU | 2094044 C1 | 10/1997 |
| WO | 2020183003 A1 | 9/2020 |
| WO | 2020183005 A1 | 9/2020 |

OTHER PUBLICATIONS

European Search Report dated Oct. 8, 2021 issued in European patent application No. 21175427.0.
International Search Report and Written Opinion dated Aug. 9, 2022 issued in international patent application No. PCT/EP2022/063745.
International Search Report and Written Opinion dated Jul. 13, 2022 issued in international patent application No. PCT/EP2022/063730.
Krause Julius et al., "The EsoCap-System—An innovative platform to drug targeting in the esophagus", Journal of Controlled Release, Elsevier, Amsterdam, NL, vol. 327, Aug. 8, 2020, pp. 1-7, ISSN: 0168-3659.
Office Action dated Mar. 5, 2026 for U.S. Appl. No. 18/561,179.

Fig. 1a
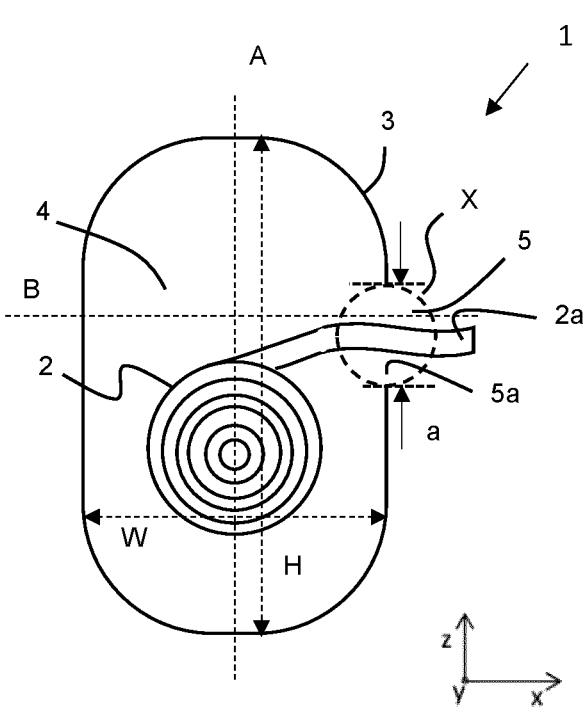
Fig. 1b                             Fig. 1c
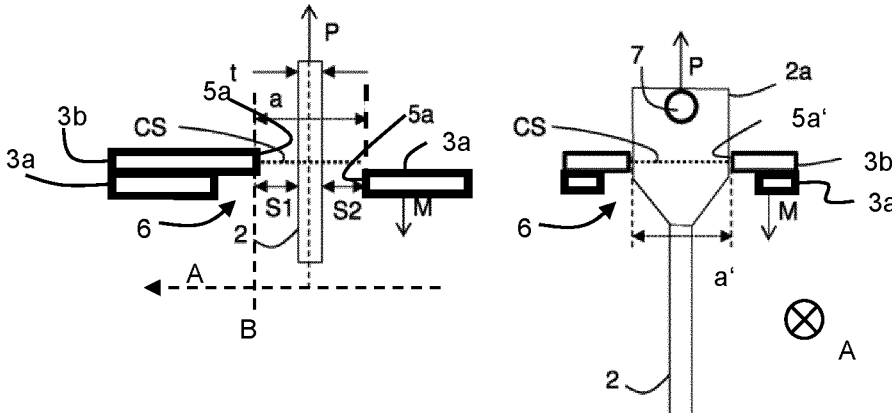

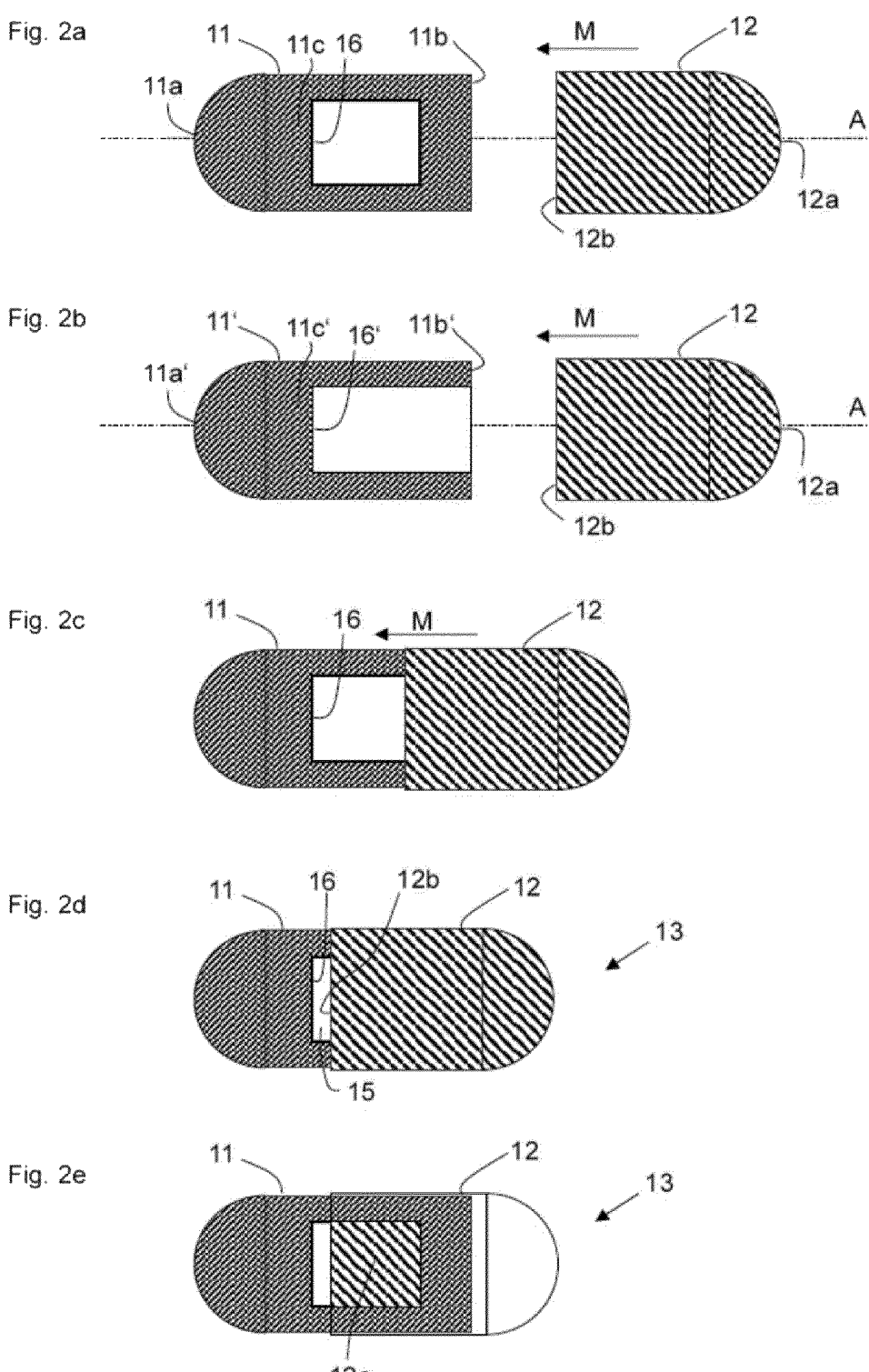

Fig. 3a
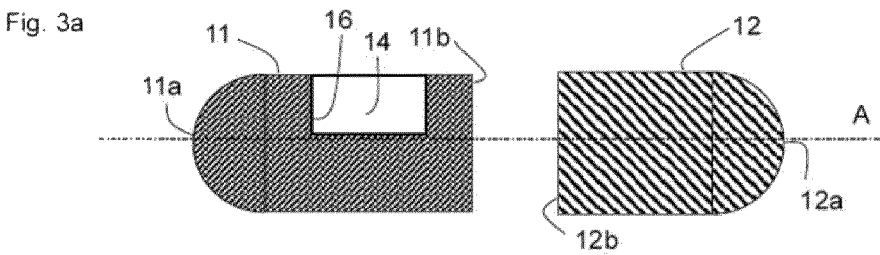
Fig. 3b
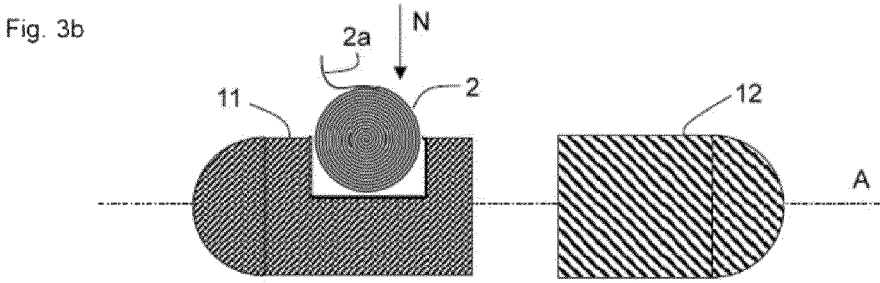
Fig. 3c
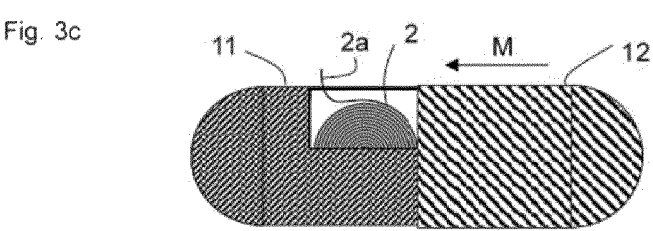
Fig. 3d                 Fig. 3e
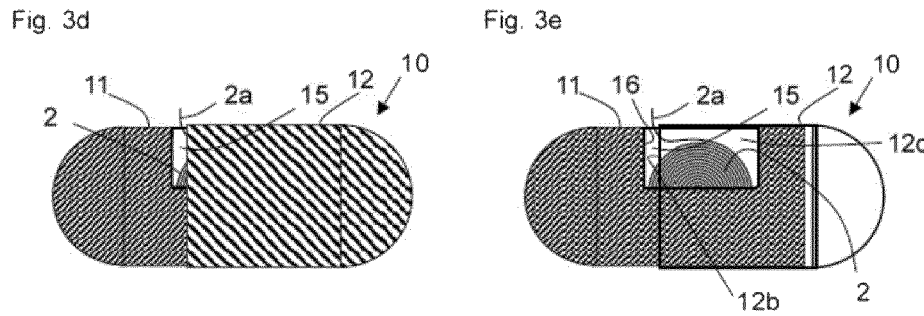

Fig. 5a                                        Fig. 5b
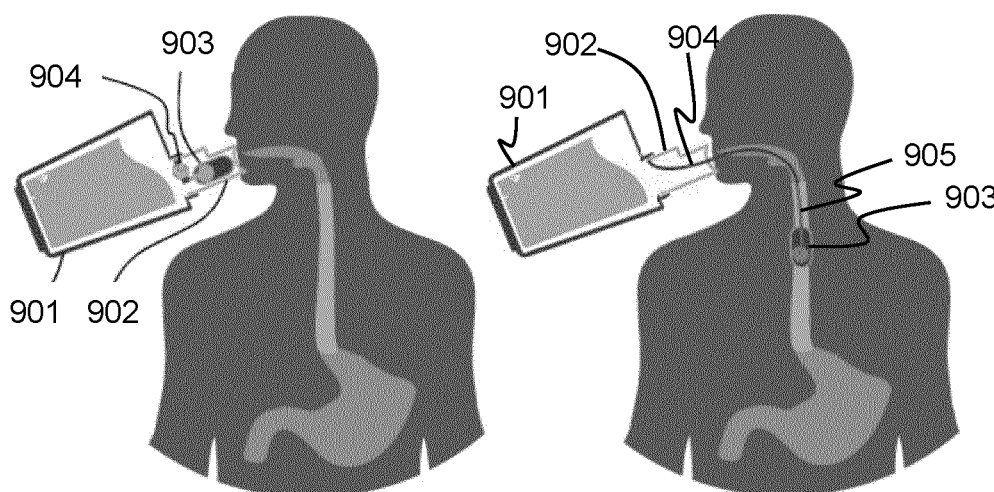

Fig. 6c
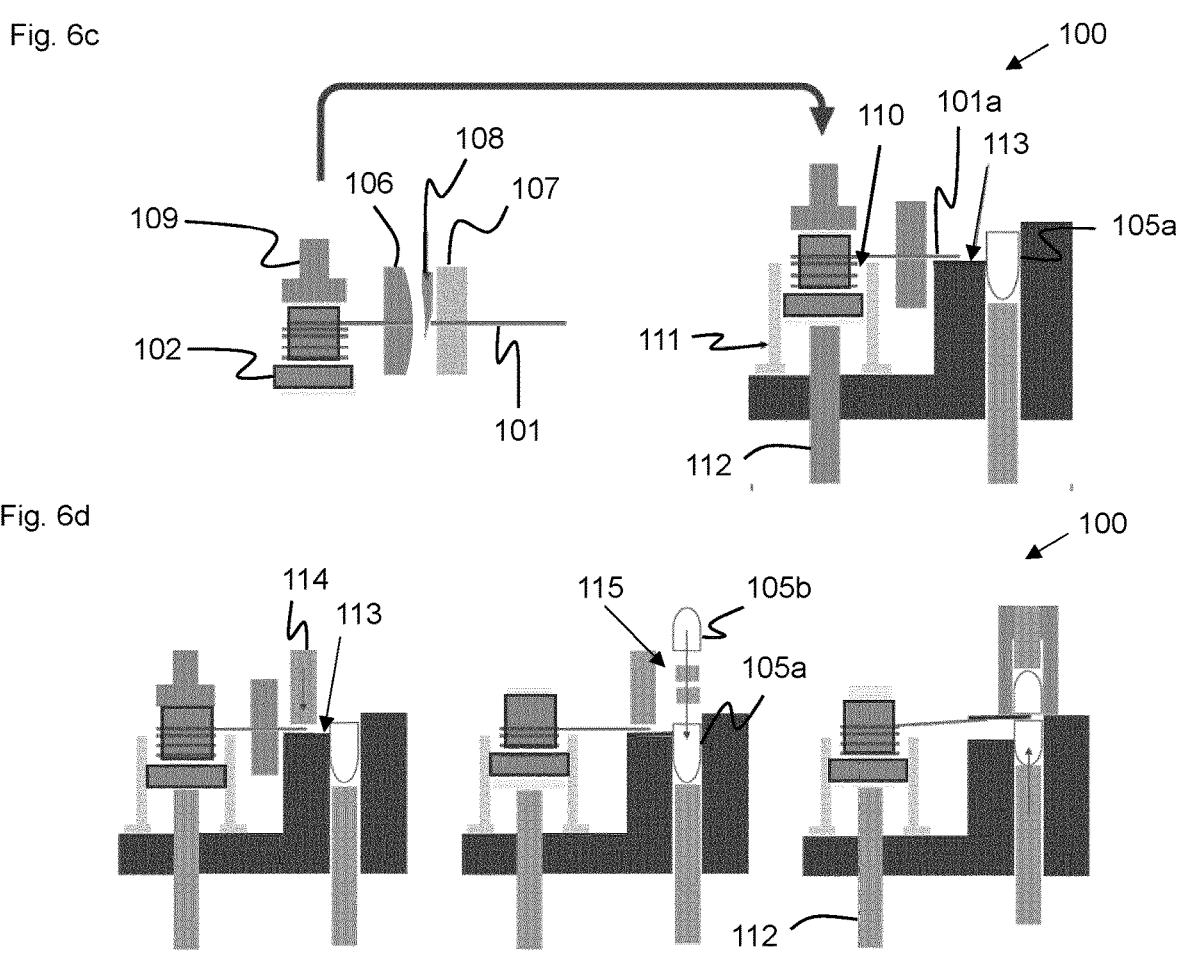
Fig. 6d
Fig. 6e
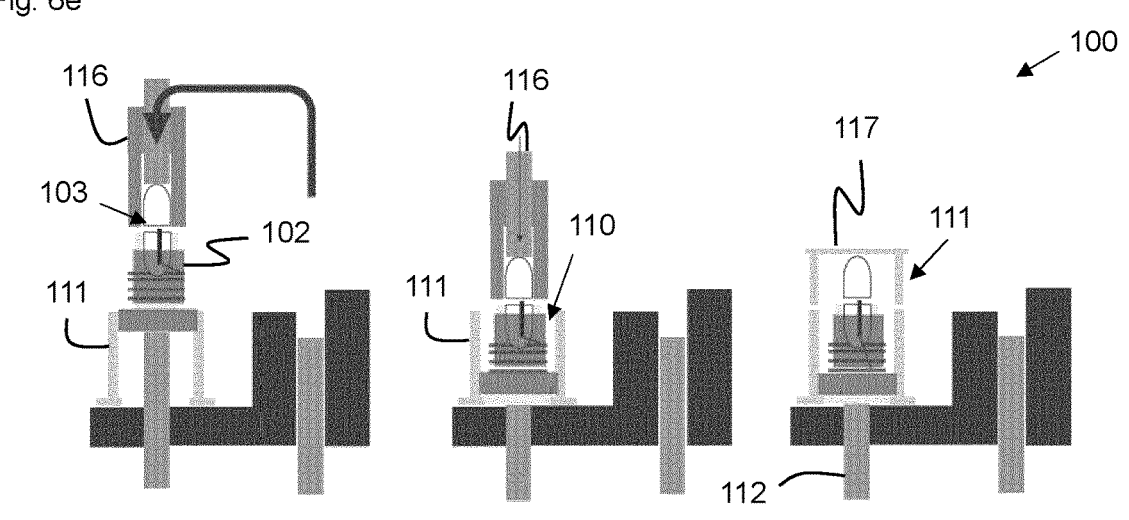

701

702 d

CAPSULE DEVICE WITH AN APERTURE FORMED BY AN OVERLAP OF TWO HALVE-CAPSULE SHELLS

RELATED APPLICATIONS

This patent application is a U.S. National Stage filing under 35 U.S.C. 371 of International Patent Application No. PCT/EP2022/063730, titled "CAPSULE DEVICE WITH AN APERTURE FORMED BY AN OVERLAP OF TWO HALVE-CAPSULE SHELLS," filed May 20, 2022, which claims priority to European Patent Application No. 21175427.0, filed May 21, 2021, each of which is incorporated herein by reference in its entirety.

The present invention relates to a capsule device and a pharmaceutical dosage form for the application to a mucous membrane, in particular to a buccal, or gastro-intestinal mucous membrane. The invention also relates to a method of producing the capsule device and the pharmaceutical dosage form comprising the capsule device.

Such capsule devices are known from WO 2020/183005 or WO 2016/102067 A1. The capsule device form of WO 2016/102067 A1 is designed such that it comprises at least one sheet like, in particular film shaped, foil shaped or wafer shaped preparation comprising the active pharmaceutical ingredient, a release mechanism, and a trigger mechanism, wherein the trigger mechanism is adapted to trigger, at a predetermined site of action, in particular of the gastrointestinal tract, of the rectum or of the vagina, the release of the sheet like preparation by the release mechanism. From the embodiment according to FIGS. 8a, 8b, 8c of WO 2016/102067 A1, a dosage form is known having an elongated, strip-shaped preparation, which comprises the active pharmaceutical ingredient, the preparation being capable to be arranged in a compact condition and in an expanded condition, the dosage form having a capsule comprising a hollow space for accommodating the compacted preparation, the capsule device having an aperture and a first end of the preparation extending, in the compact condition, through the aperture for allowing pulling out the preparation from the hollow space into the surrounding area of the capsule thereby transferring the preparation from the compact condition to the expanded condition.

It is furthermore known in the art, in particular in relation to the treatment of gastrointestinal and in particular esophageal membranes, to use catheter or stent-like devices for the topical application of active ingredient. Another approach lies in the use of liquid or gel-like media with comparably high viscosity.

The object underlying the present invention is to provide a capsule device, which can be produced efficiently, and to provide a method for efficiently producing the capsule device and a pharmaceutical dosage form, and a method for producing the pharmaceutical dosage form comprising the method of producing the capsule device.

The problem is solved by the capsule device of claim 1 and the method of producing a capsule device for a pharmaceutical dosage form according to claim 10. Preferred embodiments of the invention are subject matter of the dependent claims.

According to the invention, the capsule device, comprises a first halve-capsule shell and a second halve-capsule shell, which are joined by overlapping of the first halve-capsule shell and the second halve-capsule shell in a joined position, wherein the first halve-capsule shell has a hollow-cylindrical wall including an opening, and a wall of the second halve-capsule shell overlaps a cross-section of the opening, thereby forming the aperture of the capsule device in the joined position.

The joined position thus relates to the position in which the first and the second halve-capsule shell are telescoped, or slid into each other, thereby forming the capsule device. By pushing them partially into each other, the two halves are mechanically connected and efficiently stabilized.

The first halve-capsule shell, having the opening, acts as a vessel, which can be easily filled with the pharmaceutical preparation through the opening—or alternatively through the open end of the first halve-capsule shell. The second halve-capsule shell acts as a cover for the opening, which can be easily positioned over the opening resulting in the desired dimensioning of the aperture. The pharmaceutical dosage form according to the invention has an excellent mechanical stability, which is beneficial when the capsule is to be swallowed by a patient. Moreover, it can be efficiently produced by a method according to the present invention.

The term "halve-capsule shell" refers to the fact that the capsule device is preferably composed of two parts, which are referred to as "halves". The dimensioning, e.g., the size of the two halves can be different from each other, however, in a preferred embodiment, the two halves are dimensioned to substantially have the same dimension, i.e., the same size. The first and or second halve-capsule shells, respectively, each have a hollow-cylindrical wall, which is preferably capped by a cap portion, which has a rounded shape preferably, and in particular has the shape of a hollow half sphere. There may be at least one third part used, in addition to the first and or second halve-capsule shells, for forming the capsule device, the third part being, for example, a cylindrical or a ring element. The first and or second halve-capsule shells may be connected to each other, in the joined position, by force-fit connection and/or positive-fit connection and/or gluing or welding.

The first halve-capsule shell has a hollow-cylindrical wall, which is preferably closed at a first end and open at a second end, wherein, preferably, the opening is fully surrounded by the material of the hollow-cylindrical wall. This way, the first halve-capsule shell, in particular the wall around the opening, remains mechanically stable and provides strength to the capsule device.

As an alternative, and also preferred, the hollow-cylindrical wall of the first halve-capsule shell is closed at a first end and open at a second end, wherein the opening is formed as a recess starting at the second end and extending towards the first end. This way, the opening size can be maximized allowing for a facilitated assembling of the pharmaceutical dosage form.

Preferably, in the joined position, the first halve-capsule shell is inserted into the second halve-capsule shell. Preferably, in the joined position, the second halve-capsule shell is inserted into the first halve-capsule shell.

Preferably, a cross-section of the opening is dimensioned to receive the preparation in its compact condition before joining the first halve-capsule shell and the second halve-capsule shell, wherein preferably, in the joined position, the aperture defined by the opening and a wall of the second halve-capsule shell has a cross-section dimensioned to prevent the preparation in its compact condition from passing through the aperture. The term "cross-section of the opening" refers to the area occupied by the opening within the wall of the first halve-capsule shell. The term "cross-section of the aperture" refers to the area occupied by the aperture within the wall of the capsule device, or respectively, within the wall of the first halve-capsule shell when intersected or overlapped by the wall of the second halve-capsule shell.

In particular, the second halve-capsule shell may comprise a second opening or a second recess, which overlaps with the opening or a recess of the first halve-capsule shell, in the joined position. This way, more flexibility is gained for positioning the aperture along the length of the capsule device—said length measured along an axis A, in particular the cylinder axis A, through the capsule device.

Preferably, the size $A\_o$ of the cross-section of the aperture is a fraction f of the size $A\_a$ of the cross-section of the opening, wherein $A\_o=f*A\_a$, and wherein preferably $0.0010<f<0.7500$, preferably $0.0100<f<0.5000$, preferably $0.0100<f<0.2500$, preferably $0.0500<f<0.15000$. The area $A\_o$ is preferably adapted to allow a strip-like elongated preparation being pulled out from the aperture.

Preferably, the aperture is a slit-like aperture configured for allowing a strip-like preparation to pass through the aperture, the cross-section (CS) of the aperture being larger than the cross section of the strip-like preparation, when the latter is extending through the aperture.

Preferably, the capsule device is configured to be suitable to be swallowed by a patient.

Preferably, the capsule device comprises a sinker device, which occupies a part of the hollow space and which provides an additional weight to the pharmaceutical dosage form. In an embodiment, the sinker is arranged in one of the halve-capsule shells. Preferably, the sinker is positioned in the second halve-capsule. Therefore, the second halve-capsule comprises holding means, such as notches, to loosely position the sinker in the hollow space of the second halve-capsule, such that when the capsule is turned over, the sinker remains in the hollow space of the second halve-capsule and does not slip, e.g., due to gravity, into the first halve-capsule, e.g., to avoid the sinker from slipping onto the preparation. The notches can be created by the exterior of the capsule being constricted and curving into the interior.

The shape of the aperture preferably corresponds to the outer contours of the elongated preparation in the plane perpendicular to the length axis of the elongated preparation. For example, a slit-like aperture is preferred in case of a strip-like preparation, and a circular aperture may be provided in case of a string-like preparation. Here the aperture basically provides a rectangular passage cross-section, and the cross section of the strip-like preparation is also basically rectangular. In case of a string-like preparation, the aperture may provide a circular passage cross-section, and the cross section of the strip-like preparation may also be basically circular. This way, the motion of the elongated preparation with respect to the capsule device is guided by the aperture and the relative position of the capsule device and the preparation is stabilized while pulling out the preparation from the capsule device.

Preferably, the aperture is a slit-like aperture configured for allowing a strip-like preparation to pass through the aperture, wherein preferably, the cross section (CS) of the aperture being larger than the cross section of the strip-like preparation, when the latter is moving through the aperture. Herein, the cross-section of the aperture defines a surface, and the cross-section of the strip-like preparation is preferably measured within said surface, the strip-like preparation preferably being centered within the aperture.

The spacing S in the aperture cross section of the aperture between the elongated preparation and a surface of the capsule device defining the aperture is preferably measured when the cross section of the aperture and the cross section of the elongated preparation are centered with a virtual axis A running lengthwise through the capsule device. The dimension of the aperture resulting in a spacing S is preferably calculated by a dimension a, being a diameter or a width of the aperture, t being a diameter of a string-like preparation or a thickness of a strip of a strip-like preparation, wherein $a=t+2*S$, cf. FIG. $1c$. S is preferably ranging from 10 to 2000, or 20 to 1500, or 50 to 1000, or 100 to 750, or 200 to 500 or 300 to 400 micrometer ($\mu m$), respectively. S is larger than Null and is preferably larger than the value t, in particular $S=f*t$, f being a numerical factor chosen from 1 to 20, preferably from 2 to 15, more preferably from 3 to 12. The dimension of a is preferably chosen such that it is ranging from 100 to 4000, 100 to 2000, or 200 to 1500 or 300 to 1000, or 400 to 800 or 500 to 700, or 600 micrometers ($\mu m$), respectively.

In case of a strip-like preparation and a slit-like aperture, the length c of the passage cross section, through which the strip-like preparation passes when being pulled outwards, is larger than the width w of the strip of the strip-like preparation. The passage cross section is larger than the cross-section of the elongated preparation in the same plane.

The capsule device is generally a container being configured for a buccal, or gastro-intestinal administration, respectively. In particular, the capsule device is a swallowable object, which means, in particular, that the dimensions and the outer shape of the capsule device are suitable for swallowing the capsule device. The dimension, in particular, relates to the geometrical size of the capsule.

The first halve-capsule shell may further comprise a sliding surface, configured to guide the second half-shell when the first half-shell and the second half-shell are telescoped into each other to form the capsule device, wherein the opening of the first halve-capsule shell can additionally extend into the sliding surface, such that, when the first half-shell and the second half-shell are telescoped into each other, the opening is partially covered by the second half-shell.

The capsule device may have an elongated shape, which means that a length measured along a virtual central axis A of the capsule device is larger than its lateral outer dimension(s). The capsule device, without considering the aperture, may be rotationally symmetric with respect to the central axis A.

The capsule device may have more than one aperture, in particular two apertures, or more than two apertures.

The invention is also related to a method of producing a capsule device as defined in any of the previous claims, comprising at least the steps of:

a) Providing the first halve-capsule shell (11; 11') having a hollow-cylindrical wall (11c; 11c') including an opening (16; 16') and the second halve-capsule shell (12; 12');

b) Sliding the second halve-capsule shell (12; 12') and the first halve-capsule shell (11; 11') to a joined position, wherein a wall (12b, 12c) of the second halve-capsule (12; 12') shell overlaps a cross-section of the opening (16; 16') of the first halve-capsule shell (12; 12'), thereby forming the aperture (15) of the capsule device in the joined position, The term sliding refers to joining or telescoping the first halve-capsule shell into the second halve-capsule shell or vice versa, such that both halves reach the overlapping position to form the aperture preferably in its final state, e.g., without the need to further reduce the opening by further telescoping or joining of the two halves. This may also include a locking mechanism, e.g., means mechanical friction of a sliding surface comprised by one or both two halves, which secures both halves together, such that no further manufacturing step is necessary to join the two halves together in a manner suitable for the application in a dosage form. However, a process step, preferably carried out by machine, may also be necessary to join the halves in a manner suitable for the application, e.g., by means of heating or by welding, in particular by material bonding.

Preferably, the method of producing a capsule device comprises one or two of the following steps:

a) Providing a material for forming the capsule device, in particular the first and second halve-capsule shell;

b) Generating an opening, in particular a rectangular opening, in the material of the first and/or the second halve-capsule shell.

In the case of, for example, a circular opening, the first and second capsule halves may each have arcuate openings so that in the joined position a circle or ellipse is formed by the halves sliding together. This is advantageous if a preparation with a circular cross-sectional area is used.

The step of forming the capsule device using the material for forming a capsule device may be applied after the step of generating the opening in the material of the first halve-capsule shell. The step of forming the capsule device using the material for forming a capsule device may also be applied before the step of generating the opening in the material of the first halve-capsule device.

The opening or the recess may be generated by using a workpiece having a suitable shape, e.g. a punching tool. The material for forming a capsule device may be a workpiece. The workpiece may have, in a respectively preferred embodiment the shape of a cuboid, a foil, a hollow cylinder, a capsule or a halve of a capsule.

Preferably, the method comprises the step that the opening is generated in the hollow-cylindrical wall material of the first and/or second halve-capsule shell.

That is, the opening can be generated in the wall material of the first and/or second halve-capsule shells before forming the actual shell shape, i.e., the opening is generated in the two-dimensional material shape of which the shell shape is formed in a further step. Alternatively, the opening is generated in the halve-capsule shell, that is the opening is generated in the wall material of the first and/or second halve-capsule shells after forming the actual shell shape i.e., the opening is generated in the three-dimensional material shape which forms the shell in a step of form production.

The opening may be generated using a laser to cut or to ablate material from the capsule material. Moreover, punching may be used to generate the opening through the capsule material to create a rectangular hole via shearing. However, the opening may preferably also be created by injection molding of a suitable material, e.g., plastic, forming the capsule device. The aperture preferably has the shape of a planar curved slit. The planar property of the curved slit offers the advantage that the passage of a strip-like preparation through the slit in a pull-out direction P is facilitated, and thereby, the reliability of the mechanical process of expanding the preparation from the compacted condition to the expanded condition is further improved. If the opening in the capsule wall material is created by a punching tool, the punched-out material of the capsule wall can be transported away from the capsule by a suction device, which is ideally integrated in the punching tool, e.g., by under pressure suction.

The capsule device is preferably formed such that, when a preparation having an elongated shape and comprising the active pharmaceutical ingredient, is inserted in a compact condition of the preparation inside a hollow space of the capsule device and an end portion of the preparation is extended through the aperture, and the preparation being capable to be pulled out from the aperture, a spacing is provided in the aperture cross section (CS) of the aperture between the preparation and a surface of the capsule device defining the aperture. The capsule device is preferably formed to be swallowable by a patient.

The step of forming the opening may comprise at least one of the following features:

using a planar milling tool, e.g., a planar saw blade, or by another tool resulting in a plate-shaped cutting volume, e.g., a cylindrical milling head performing a lateral motion;

using a laterally moved waterjet in process of abrasive waterjet cutting;

using a laser to cut or to ablate material from the capsule material;

punching through the halve-capsule shell material to create a hole via shearing;

injection molding of a suitable material, e.g., plastic, for forming the halve-capsule shell.

The step of forming the capsule device may comprise the step of applying a dip molding process, for producing two halve-capsule shells of a capsule device which are joined to form the capsule, as for example, basically described in EP0102832A2. The step of forming the capsule device may comprise the step of applying a process of additive manufacturing for forming the capsule from a suitable material, in particular a 3D-printing process for forming the capsule from a suitable material. The step of forming the capsule device may comprise the step of injection molding a capsule from a suitable material.

The capsule device may be a capsule, including a hollow cylinder, which is capped on both sides by curved cap members. A cap member may have basically the shape of a semi-sphere. A cap-member may be manufactured with a cylindrical portion as one piece. Two parts of a capsule device may be joined to form the capsule device—this facilitates assembling the dosage form by first placing the preparation inside one of the two parts, and then securing the preparation by joining the two parts of the capsule device. A capsule may also be shaped to have an elliptical or oval cross section, such that the capsule has the shape of an olive, for example.

In a preferred embodiment, the capsule device is configured such that the aperture is offset from the central axis A, which means that the central axis A does not cross the aperture cross section, or which means that the central axis A does not cross a central point of the aperture cross section. An advantage of such an embodiment is that the force acting on the wall of the capsule device, when the preparation is pulled out from the capsule device and the capsule device is administered to a patient, is reduced and the risk of damaging the capsule device is thereby reduced. In experiments of the inventors, it was found that, in particular for a strip-like preparation, the unwinding of a rolled preparation through an aperture—being arranged offset from the central axis A—is facilitated compared to a central position of the aperture, the central position being such that the central axis A of the capsule device runs through a center of the aperture.

In case of a slit-like aperture, the aperture is preferably arranged offset from the central axis A of a capsule device. The slit is preferably formed by opposing surfaces of the walls, which form the capsule device.

For example, the preferred shape of a slit is achieved when initially preparing the opening by milling off the cylindrical wall, which forms the first halve-capsule shell, such that a plate-shaped volume is subtracted from the wall—when considering the first halve-capsule shell and the cut volume to be three-dimensional mathematical objects. The orientation of the plate-shaped volume subtracted from the capsule material is characterized by the orientation of the main plane of the plate-shaped volume, in particular with respect to the direction of the virtual central axis A of the capsule device.

The hollow space inside the capsule device is defined by at least one inner wall of the capsule device, in particular the first and second halve-capsule shells.

In a preferred embodiment, the capsule device is defined by at least one wall, which has an outer side, facing the surrounding of the capsule device and having an inner side facing the hollow space. Preferably, the inner side (inner surface) and the outer side (outer surface) run in parallel to each other, which means that the outer contour surface of the hollow space is similar to the outer contour surface of the capsule device. However, it is also possible and preferred that the inner surface of the capsule device is at least portion-wise not in parallel to the outer contour surface of the capsule device. Such a configuration allows defining auxiliary structures inside the capsule device, which assist in guiding the motion of the preparation inside the capsule device or other function.

Preferably, the auxiliary structure is an inner guiding wall of the capsule device, which is arranged for guiding the uncoiling and/or unwinding of the preparation inside the capsule device. The guiding wall is arranged for guiding the positioning of the preparation during uncoiling and/or unwinding of the preparation. The guiding wall may be arranged in parallel to the direction P of the movement, by which the preparation is moved inside the capsule device towards the aperture. Preferably, the guiding wall is arranged to be aligned with the aperture, e.g., the guiding wall is preferably parallel to the longitudinal orientation of the aperture, that is parallel to the Y-direction as defined in FIG. 1a. The guiding wall may also be realized by protrusions within the area of the inner wall of the capsule device, where the preparation is positioned to be unrolled through the aperture. Such protrusions in the wall of the capsule device, or notches when seen from outside the capsule device, can serve to guide the preparation during unrolling, e.g., by the inner part, i.e., the core of the rolled preparation being mechanically supported by the protrusions so that it can rotate, especially during the unrolling movement of the preparation.

Preferably one or more inner walls of the capsule device are arranged to form a guiding compartment inside the capsule device. The guiding compartment is arranged to support the preparation in its compact condition and assists in unwinding the preparation. Preferably, the one or more inner walls of the capsule device are arranged to form side walls of a cuboid hollow space, which accommodates the preparation in its compact condition.

Preferably, the capsule device comprises a guiding member, which is arranged inside the inner space of the capsule device to guide the motion of the string-like or sheet like preparation towards the aperture of the capsule device. The guiding member may be a part of the inner wall of the capsule device or a part, in particular a wall member, being supported by the inner wall of the capsule device or being connected to the inner wall of the capsule device. The guiding member can, for example, be a guiding lip or a guiding spout arranged on one side of an edge of the aperture, or it can be mounted all the way around the aperture or the opening.

Preferably, the capsule device may contain an auxiliary structure being configured to guide a coiling and/or uncoiling of a string-like preparation or a winding and/or unwinding of a strip-like preparation, in particular by coiling or winding the preparation around one or more rods or cylinders of the auxiliary structure. The rod or cylinder may be rotatably disposed inside the capsule device for facilitating uncoiling or unwinding.

In another preferred embodiment, the capsule device as well as the pharmaceutical dosage form respectively comprise a sinker device. The sinker device is configured to provide negative buoyancy to the capsule device. In experiments of the inventors underlying the finding of this preferred embodiment it was found that reducing the buoyancy, for example by increasing the mass of the capsule device, leads to an improved swallowability of the capsule device, i.e., an improved reliability of the mechanical process of expanding the preparation from the compacted condition to the expanded condition. In case of strip-like preparation, the unwinding of the preparation from the compacted condition, where the strip-like preparation is wound around a winding axis, to the expanded condition was significantly facilitated and more efficient. For example, such a sinker is described in WO 2020/183005 A1.

The invention also relates to a pharmaceutical dosage form, comprising the capsule device as herein defined and which further comprises a pharmaceutical preparation with an elongated shape and which comprises one or more active pharmaceutical ingredients, and which is capable of being arranged in a compact condition and in an expanded condition.

The invention is also related to a method of producing a pharmaceutical dosage form, wherein the method comprises the steps of the method of producing a capsule device according, and the following further steps:

a) Providing the preparation having an elongated shape and comprising one or more active pharmaceutical ingredients;

b) Providing the first halve-capsule shell having a hollow-cylindrical wall including an opening and the second halve-capsule shell;

c) Accommodating the preparation, preferably in a compact condition, through the opening into the first halve-capsule shell, such that a part or an end of the preparation extends through the opening;

d) Sliding the second halve-capsule shell over the first halve-capsule shell or sliding the first halve-capsule shell over the second halve-capsule shell to a joined position, thereby reducing the cross-section of the opening, while the end of the preparation extends through the opening, until the opening forms the aperture of the capsule device in the joined position of the first and second halve-capsule shells.

Preferably, the method comprises the following step:

After step a) or b) of the method of producing a pharmaceutical dosage form, providing a rotation axle (X), and, preferably, positioning the same in front of the opening or within the cross-section of the opening, and winding the preparation in its elongated condition by rotating the rotation axle, thereby preferably using the opening for guiding and/or aligning the preparation, until the preparation has reached a wound and compact condition. This way, any problems related to unwinding of the preparation before reaching the interior of the capsule may be reduced or eliminated, because the compact form of the preparation is formed within the opening and the interior of the first halve-capsule device.

Preferably, the method of producing a pharmaceutical dosage form comprises the following step:

after step b) or c) of the method of producing a pharmaceutical dosage form, positioning a sinker device within at least a part of the hollow space of the first and/or the second halve-capsule shell, the sinker device providing an additional weight to the pharmaceutical dosage form. This may, in particular, facilitate swallowing of the pharmaceutical dosage form.

Preferably, any of the method steps, and in particular loading of the preparation in its compact form into the first halve-capsule shell, are performed automatically by a machine, to preferably produce multiple pharmaceutical dosage forms in parallel. Thereby the throughput for producing a high quantity of pharmaceutical dosage form per time period is enhanced.

The step of placing or accommodating the preparation having an elongated shape and comprising the active pharmaceutical ingredient, in a compact condition of the preparation, inside a hollow space of the capsule device and letting an end portion of the preparation extend through the aperture, comprises the aperture and the preparation being configured such that, when the preparation is pulled out from the aperture, a spacing is provided in the aperture cross section (CS) of the aperture between the preparation and a surface of the capsule device defining the aperture.

The step of placing the preparation is performed, preferably, by placing the preparation in the first part or first halve-capsule shell, preferably followed by letting the end portion of the preparation extend through the aperture, and by connecting the second part, or second halve-capsule shell, to the first part or first halve-capsule shell. The first part or first halve-capsule shell or second part or second halve-capsule shell, respectively, may be a tube element or capped tube element or may be a cylinder segment, in particular a half-cylindrical element.

The invention also relates to a kit comprising a pharmaceutical dosage form according to claim 13, a drinking cup, and an applicator for administering the pharmaceutical dosage form to a patient, wherein the applicator is in fluid connection with the drinking cup and comprises the pharmaceutical dosage form and wherein the preparation of the pharmaceutical dosage form is connected to the applicator by a retainer for withdrawing the preparation from the capsule device after administration to the patient.

The capsule device and pharmaceutical dosage form comprising the pharmaceutical preparation according to the invention is particularly suited for the application to a mucous membrane, in particular to buccal or gastrointestinal mucous membranes, in particular to a mucous membrane within the upper gastrointestinal tract such as throat, esophagus, cardia and/or stomach. A pharmaceutical dosage form comprising a pharmaceutical preparation and its application is described in WO2016/102067, which is incorporated by reference herein in full, in particular in with regard to the shape, size and (chemical) composition of the capsule device and the pharmaceutical preparation, the active pharmaceutical ingredients and the treatment and prophylaxis of certain conditions and diseases already disclosed therein. Stated differently, the chemical constituents of the capsule device and the pharmaceutical preparation as such are at least to a significant extent already described in said reference. The same applies to the capsule.

The pharmaceutical dosage form of the present invention advantageously allows improving the bioavailability of active pharmaceutical ingredients at a predetermined site of action.

The pharmaceutical dosage form of the present invention is capable of and adapted to rapidly release a string-like or strip-like, in particular a sheet-like, film-shaped, foil-shaped, or wafer-shaped, pharmaceutical preparation comprising the active pharmaceutical ingredient at a predetermined site of action with a systemic effect. Furthermore, the pharmaceutical dosage form according to the present invention makes it possible to apply active pharmaceutical ingredients, which cannot be administered orally due to poor bioavailability, at a predetermined site of action.

The string-like or strip-like, in particular film shaped, foil shaped or wafer shaped, preparation that comprises the active pharmaceutical ingredient, may comprise a single- or a multi-layered structure of multiple layers. In case of a multi-layered structure, a first layer may contain a first active pharmaceutical ingredient and a second/further layer may contain at least a further active pharmaceutical ingredient. This allows the application of, e.g., two pharmaceutical ingredients, which are as such not compatible with each other.

Preferably the preparation is made mucoadhesive in order to allow the targeted release of the active ingredient. This may be achieved by providing a single layer, which, besides comprising the active pharmaceutical ingredient, is made mucoadhesive, or by providing the preparation in the form of a multilayer, wherein at least one, preferably the outermost layer is made mucoadhesive.

According to a preferred embodiment, the pharmaceutical dosage form according to the present invention is adapted to be orally administered.

The capsule device consists of or mainly consists of a material that is essentially insoluble in a fluid which is present at the path of transporting the same to the site of administration, in particular of the gastrointestinal tract. Such materials are known in the art and described in WO2016/102067. In particular to be mentioned are the known gastric juice-resistant polymer, such as polymethacrylates (Eudragit), HPMCAS, shellac, gelatin, etc., which may be formulated together with known additives for improving processability, such as plasticizers; fragrances and flavorings.

The preparation comprises at least one active pharmaceutical ingredient (the drug name also includes any pharmaceutically acceptable salt thereof) selected from the group of:

diagnostics substances such as dyes or stains, analgesics, preferably NSAIDs, such as ibuprofen or flurbiprofen;

local anesthetics such as benzocaine, butamben, dibucaine, lidocaine, oxybuprocaine or novocaine;

antibiotics such as penicillin, amoxicillin or vancomycin; antiseptics such as 2,4-dichlorobenzyl alcohol, amylmetacresol or cetylpyridinium chloride;

steroids such as corticosteroids, glucocorticoids, fluticasone, budesonide, clocortolone, perdesonide, hydrocortisone, clobetasonbutyrate, flumetason, fluprednidone, hydrocortisone aceponate, hydrocortisone buteprate, hydrocortisone-17-butyrate, triamcinolonacetonid, amcinoid, betamethason-17,21-dipropionate, betamethason-17-valerate, desoximetasone, diflucortolon-21-valerate, fluocinolonacetonid, fluocinonid, fluticason-17-propionate, methylprednisolone aceponate, mometasonfuroat, pednicarbat or clobetasol-17-propionate;

parasizides, which are also called parasiticides, such as mebendazole, albendazole, tiabendazole, diethylcarbamazine, diaminodiphenyl sulfone, benznidazole, ivermectin, pyrantel, praziquantel;

fungicides such as nystatin, imidazole, triazole, thiazole, clotrimazole, ketoconazole or undecylenic acid;

hexamethyl pararosaniline chloride, Amphotericin B, botulinum toxin, sucralfat, nitric oxide, or nitric oxide forming agents such as isosorbide dinitrate or nitroglycerine, furanocoumarins, benzoic acid, citric acid, lactic acid, pH buffers, antacids, calcium carbonate, magnesium carbonate or aluminum carbonate.

Additionally or alternatively, the preparation particularly can comprise an inflammation regulator such as montelukast, interleukin receptors or interleukin antibodies. Additionally or alternatively, the sheetlike preparation particularly can comprise beclomethasone dipropionate, budesonide or ciclesonide, which are particularly beneficial for asthma therapy. Additionally or alternatively, the sheetlike preparation particularly can comprise mesalazine, sulfasalazine or olsalazine, which are particularly beneficial for treating inflammatory bowel disease.

An active pharmaceutical ingredient contained in a sheetlike preparation of the pharmaceutical dosage form according to the invention may, in particular, be selected from the group comprising proteins and peptides, in particular insulin, buserelin, oesmospressin, calcintonin and estrogen as well as biotechnologically manufactured drugs such as antibodies, e.g. rituximab. Here, it is to be understood that proteins and peptides, in particular insulin, buserelin, desmopressin, calciotonin and estrogen may display, under certain circumstances, a bad—in particular a bad oral—bioavailability and thus are good candidates for the application by means of the dosage form according to the present invention.

Substances from the following groups may also be used as active pharmaceutical ingredients: drugs acting on the skeleton and the muscles, drugs acting on the nervous system, hormones and drugs acting on the hormonal system, gynecologic acting drugs, drugs acting on the cardio-vascular system, drugs acting on the respiratory system, drugs acting on the gastrointestinal tract, diuretics, drugs acting on the sensory organs, dermatics, vitamins and micronutrients, peptide based drugs and proteins, analgesics, anti-infectives, and parasizides.

In one embodiment, the active ingredient is selected among corticosteroids. Exemplarily budesonide, mometasone, fluticasone and ciclesonide, and pharmaceutically acceptable salts thereof are to be mentioned.

As to the conditions to be treated exemplarily those related to the gastrointestinal mucosa, preferably the esophagus, such as GERD, NERD as well as eosinophilic esophagitis are to be mentioned, which are particularly well treated with the above mentioned groups of steroids and the mentioned nitric oxide or nitric oxide forming agents.

The pharmaceutical preparation contains the active pharmaceutical ingredient in an amount know to be effective for the condition to be treated and depend upon site of administration and active ingredient. For, e.g. budesonide the concentration/amount within the dosage form is significantly higher compared to mometasone containing dosage forms.

Additionally, or alternatively, in certain embodiments of the capsule device according to the present invention the string-like or strip-like preparation is adapted to dissolve, e.g., to bio-degenerate, preferably in a time-controlled manner, e.g., within one hour, or within one to two hours or within one to five hours, or within one to twelve hours, or within one to twenty-four hours. This improves the user convenience as the sheet like preparation does not need to be removed.

The way of preparing a preparation containing these active ingredients is not particularly limited and known to the skilled person. Again, in relation to pharmaceutical dosage forms of the present invention, reference is made to WO2016/102067.

The, in particular the string-like or strip-like, preparation can be prepared by a person skilled in the art by basically known methods, for example by coating of an inert support with a liquid composition which comprises the polymer(s), active pharmaceutical ingredient(s) and optionally additive(s) and solvent(s), by means of, e.g. a method involving a doctor blade, spray processors or extrusion processors. The thin film layer obtained in such a way is dried. For a multi-layered sheet like preparation one or more coatings may be applied onto the existing film layer in the same manner or may be manufactured separately and then be subsequently laminated.

The shape of the aperture preferably corresponds to the outer contours of the elongated preparation in the plane perpendicular to the length axis of the elongated preparation. For example, a slit-like aperture is preferred in case of a strip-like preparation, and a circular aperture may be provided in case of a string-like preparation. Here the aperture basically provides a rectangular passage cross-section, and the cross section of the strip-like preparation is also basically rectangular. In case of a string-like preparation, the aperture may provide a circular passage cross-section, and the cross section of the strip-like preparation may also be basically circular. This way, the motion of the elongated preparation with respect to the capsule device is guided by the aperture and the relative position of the capsule device and the preparation is stabilized while pulling out the preparation from the capsule device.

Preferably, the string-like or strip-like preparation is bendable such that it can convert from a compact form, in particular with a folded, collapsed, coiled, rolled or coiled up sheet like preparation that may preferably have a string like, cord like, strip like or tube-like shape, to the expanded form. For example, such a sheet like preparation is exemplarily described in the following application WO 2020/183005.

In a preferred embodiment of the capsule device, for withdrawing the preparation contained in the capsule from the hollow space of the capsule into the surrounding area of the capsule device, the preparation is expandable from a compact form to an expanded form. Therefore, the preparation preferably comprises a holding device. Upon fixation of the holding device, the preparation can be withdrawn from the capsule device by a pulling movement and/or force. Fixation of the holding device is obtained by preferably connecting the holding device to a retainer. Such a retainer can be a string member, as for example, a cord, string, tether. The retainer then, for example, retains the holding device from moving along with the capsule device, thereby creating a pulling force. Fixation is made, for example, by connecting the holding device to one end of the cord, whereas the other end of the cord is secured in an applicator. Therefore, when the retainer cord is tensioned by moving the capsule away from the applicator, the holding device establishes a pulling force, such that the preparation is pulled out of the capsule device. As the holding device is preferably a part of or is attached to the preparation, the holding device can be a handle, sling or adhesive tape or may comprise an adhesive region. The holding device is adapted to build up and maintain a connection that can transfer a force between the holding device and a region where it is attached. Furthermore, this connection may be built up or maintained, while the dosage form and/or the sheet like preparation is in its compact form and/or its expanded form. Preferably, the holding device may hold itself, and possibly further parts, at a defined position or region by a force fit, in particular in a frictionally engaged manner, form-fittingly or by material engagement, in particular by mucoadhesion, preferably by an adhesive bond. For example, such a holding device is described in WO 2016/102067 A1.

The term "compact form" as used herein preferably refers to a folded form, coiled form, rolled form, coiled up form or collapsed form. In particular, a string-like or strip-like preparation has a smaller spatial extent and/or exposes a smaller amount of its surface in a compact form than in a form that is not a compact form, particularly in an expanded form. Preferably, a string-like or strip-like preparation in a compact form is folded, collapsed, coiled, rolled, coiled up, compressed, lumped together or brought into a smaller format in another way. In particular, a string-like or strip-like preparation can have a predetermined size or spatial extent, when it is in a compact form.

The term "expanded form" as used herein preferably refers to an unfolded form, spread out form, opened up form, elongated form, stretched form or oblong form. In particular, a string-like or strip-like preparation has a greater spatial extent and/or exposes a greater amount of its surface in an expanded form than in a form that is not an expanded form, particularly in a compact form. Preferably, a string-like or strip-like preparation in an expanded form is unfolded, spread out, opened, unrolled, uncoiled, opened, elongated, stretched, expanded or brought into a bigger format in another way. In particular, a string-like or strip-like preparation can have a predetermined size or spatial extent, when it is in an expanded form. Alternatively, the size or spatial extent of a string-like or strip-like preparation may depend on the conditions present and a site of action or application site, and thus may not be predetermined.

In a particularly preferred embodiment, the preparation is wound outside the capsule device. In such a case, for example, it is intended to position the preparation in its compact form inside the first half capsule shell and only subsequently to connect the second half capsule shell to the first half capsule shell to form the capsule device.

However, alternatively, the preparation is wound inside the capsule device. If wound inside the capsule device, the preparation is advantageously provided in its expanded condition from outside the preparation and fed into the capsule device, e.g., through the opening and/or the aperture of the capsule device during winding. In such a case, the capsule device preferably is provided with the first halve-capsule shell having a hollow cylindrical wall including an opening, and a wall of the second halve-capsule shell overlaps a cross-section of the opening. However, the two halves are not necessarily overlapping such that the aperture is finally formed. Alternatively, the wall part used for covering the opening to form the aperture is preferably not provided during, but after winding is finished.

Preferably winding of the preparation is made by machine, e.g., means a winding device or unit. Alternatively, the preparation can be wound manually. During manual as well as machine winding of the preparation, an end section of the preparation is for example clamped between two holding jaws, or if an essentially continuous preparation is used, a section of the preparation is clamped and the part outside the clamped section is cut off, so that the clamped section of the preparation forms an end section of the preparation to be wound. Further exemplary, the clamped section of the preparation is braided into the fork or U-shaped end of a winding pin so that the preparation is wrapped around the end of the pin by rotating the pin. Subsequently, the pin with the preparation wrapped around it is deposited, for example through the opening in the capsule device, and the pin is pulled out of the wrapped preparation. In a particularly preferred embodiment, the coiled preparation is positioned in the first halve-capsule shell through the opening.

Alternatively, the preparation is fed in its expanded condition via a conveyor, e.g. a conveyor belt, into a pressing chamber. A number of surfaces rotating preferably in a common direction are arranged at the inside of the pressing chamber, which cause the drawn-in and yet unfolded preparation to rotate. In addition, the rotational movement of the preparation can be supported by rollers. The principle is similar to that of a baler. The rotational movements of the rotating surfaces inside the pressing chamber are transmitted to the preparation, so that the preparation itself is set into a rotational movement and thus begins to coil. As soon as the preparation has a predetermined size and/or weight, the rotary movement stops and the wound preparation is ejected from the pressing chamber and, for example, directly into the opening of the capsule device.

The machine for winding the preparation into a compact form has a balance so that by measuring the weight during the winding process or by measuring the weight of a section of the preparation intended for winding, an amount of active substance which the preparation contains can be determined. Alternatively, a device that measures the length, or the wideness or the thickness or any combination of these quantities, e.g., the volume, of the portion of the preparation to be wound can be used. In case of further alternatives, it must be possible to determine the concentration of the active ingredient of the preparation present in the compact form.

The invention is also related to a production machine for producing the pharmaceutical dosage form according to the invention, in particular by executing the method according to the invention, the production machine comprising, a positioning device for positioning the first halve-capsule shell in a mounting position.

A connection device having a movable element configured for connecting the second halve-capsule shell and the first halve-capsule shell to a joined position by moving the first and second halve-capsule shells towards each other, such that a wall of the second halve-capsule shell overlaps a cross-section of the opening by an amount controlled by the movement of the movable element thereby forming the aperture of the capsule device in the joined position.

The positioning device, preferably, comprises one or more holding members, for holding one or more of the first halve-capsule shells and/or the second halve-capsule shells in place. The holding member preferably comprises a retaining space, which is shaped to retain the first halve-capsule shell and/or the second halve-capsule shell by a positive fit connection. The positioning device, in particular the holding member, may be configured to hold a plurality of first and/or second halve-capsule shells in place in parallel. This way, the throughput of the production method can be increased. The positioning device may provide for positioning one or more of the first halve-capsule shells and/or the second halve-capsule shells in more than one mounting positions. Thereby, several steps of the production of a pharmaceutical dosage form can be performed in parallel using the plurality of mounting positions, in particular working stations.

The positioning device preferably comprises a movable platform carrying one or more working stations. A working station, preferably, comprises at least one or more holding members. A movable platform may be rotatably arranged at a base member for rotating around an axis, configured for rotating each working station to a working position of the production machine. At a first working position, a feeding device for feeding at least one first halve-capsule shell to at least one mounting position provided by at least one holding member may be arranged. At a second working position, a feeding device for feeding at least one second halve-capsule shell to at least one mounting position provided by at least one holding member may be arranged. At a third working position, an equipment device may be arranged for equipping a first halve-capsule shell with a preparation, preferably in its compact condition, the equipment device possibly comprising a transport device for transporting at least a part or the whole of a preparation to the mounting position, and/or comprising a compacting device, in particular a winding device, for transferring the preparation from an elongated condition to a compact condition, in particular a folded or wound condition. At a fourth working position, a reception station may be provided for receiving the readily produced pharmaceutical dosage forms, and possibly forwarding the same to a storage or a conveyor system.

Preferably, the production machine comprises a transport device for transporting an end of a preparation, which has an elongated shape and comprises an active pharmaceutical ingredient, from a storage position of the preparation to a mounting position, where the preparation is positioned to be inserted into the hollow space of the first halve-capsule shell, which is in the mounting position, in particular to be inserted through the opening. In a preferred embodiment, the transport device has a rotatable transport member, which is configured to receive at least a part of a preparation or the whole preparation at a first position, in particular from a preparation storage device, and to transport said at least part of the preparation to the mounting position by rotation. The rotatable transport member may be a rotatable bar member or disk member. The movement or rotation of the transport device may be controlled by an electronic control device of the production machine. The production machine and/or the rotatable transport member comprises a winding device for winding the preparation from its elongated condition to its compact position. The rotatable transport member may comprise a winding device for winding up a preparation in its elongated condition to form a wound condition. The winding device may comprise one or two, or more, rotatable axles, which are configured to be electrically driven and controlled by an electronic control device of the production machine. One or two, or more, rotatable axles may be arranged at positions offset form the rotation axis of a rotatable transport member. The rotatable transport member and/or the winding device may be configured to wind up a preparation in its elongated condition in the mounting position, in particular if the rotatable axle is positioned in front of the opening or within the opening, such that the formation of the preparation in its compact condition takes place in a compacting position, which is preferably located in front of the opening or even within the opening, —and thereby, preferably, at least in part directly within the hollow space of the first halve-capsule shell, —when the first halve-capsule shell is in the mounting position. Thereby, transferring of the preparation into the capsule is remarkably facilitated. Winding of the preparation is preferably made by use of the winding pin. Therefore, the winding device preferably comprises a winding pin.

Preferably, the production machine and/or the transport device comprises a compacting device, in particular a winding device for winding the preparation from its elongated condition to its compact position or a folding device for folding the preparation from its elongated condition to its compact position. This compacting takes place, preferably, in a compacting position of the production machine.

Preferably, the production machine comprises a cutting device for cutting the preparation to form the preparation, which is to be inserted into the hollow space of the first halve-capsule shell.

Preferably, the production machine comprises an actuation device for moving the preparation in its compact condition from the compacting position to its end position inside the hollow space of the first halve-capsule shell.

Preferably, the production machine further comprises a pressing device, for pressing a sinker material, e.g., a powder, such that the sinker device is obtained. Preferably, the pressing device is configured to feed the obtained sinker device to the further processing devices for producing the pharmaceutical dosage form.

In an embodiment, an applicator to assist swallowing the capsule device in combination with a drinking cup, may be used for administration. For example, such an applicator is described in WO2020/183003A1. This is particularly beneficial, if the dosage form is to be administered on a regular, in particular daily, basis as administration of the capsule device is then possible without professional help.

The applicator comprises a housing and a capsule holder configured to accommodate the capsule device. The applicator preferably further comprises a spacer. In an embodiment of the applicator, the applicator is not directly attached to an opening of a drinking cup. Instead, the spacer is positioned between the drinking cup and the applicator. The spacer thereby reduces the risk of moisture from the drinking cup before use rendering the dosage form unusable. For example, by residual moisture of the drinking cup getting into the applicator. The space preferably has the shape of a tube or has an annular shape and preferably is screwed onto the opening of the applicator and the drinking cup respectively, after the corresponding caps have been removed. The spacer preferably has a length of 1 to 10 mm, preferably of 2 to 8 mm, most preferably of 5 mm.

The invention also relates to a retainer. The retainer is part of the applicator, in that the applicator further comprises the retainer. In a preferred embodiment the retainer consists of or comprises a string element. The retainer is wound around the capsule holder. The capsule holder therefore comprises a wall structure. The retainer is preferably attached to or fixed at the capsule holder, such that the retainer can transmit a force, e.g., a mechanical traction force to the capsule holder and thus to the applicator. The retainer is preferably made of or comprises a yarn, or a fiber or a string or a thread, having a first end and a second end. With its first end the retainer is connected to the one end of the preparation, e.g., to the holding device of the preparation, which extends through the aperture of the capsule device. With its second end the retainer is connected to the capsule holder of the applicator, e.g., the wall structure of the capsule holder. As the retainer is connected to the preparation, the retainer unwinds from the capsule holder when the capsule is moved away from the applicator and the retainer is tensioned. As the patient swallows the capsule, it is moved away from the capsule holder thereby unwinding the retainer from the capsule holder. When the patient swallows the capsule, the retainer will be completely unwound from the capsule holder at some point in time and a tensile stress will built up which pulls the preparation out of the capsule. Therefore, the retainer, e.g., a string member, advantageously allows releasing the active pharmaceutical ingredient, in particular to mucous membranes that enclose a rather small lumen or cavity such as the esophagus or nasal cavity.

Before usage of the applicator, the retainer is wound around the wall structure of the holder. By wrapping the retainer around the holder, knots are prevented from forming in the retainer. When the patient swallows the dosage form, the retainer is unwound from the holder.

Winding of the retainer around the structure of the holder and/or bonding of the retainer to the preparation, e.g., to the string comprising the preparation, or to the holding device of the preparation, is preferably made by machine, e.g., by a winding and/or bonding machine, in particular in a bonding area of the machine.

In a first step for wrapping the retainer around the holder, the retainer is mechanically fixed in a machine, e.g., clamped by support jaws. In a second step the retainer is tensed. In a third step the holder is positioned along the tensed retainer means a mechanical clutch and the retainer is clamped in a groove of the wall structure of the holder. In a fourth step the support jaws for clamping the retainer are opened. In a fifth step, the holder is rotated by rotating the clutch that fixes and supports the holder, thereby wrapping the retainer around the holder. The rotational movement of the coupling is superimposed on a vertical translational movement, so that the retainer is wound onto the holder in juxtaposed positions. In a sixth step, the support jaws fix the retainer again and in a seventh step, a knife-like component of the machine cuts through the one end of the retainer, which is connected to the preparation in the further steps. In an eighth step, the holder with the retainer wrapped around it is positioned over the opening of the applicator housing, in particular by machine, and preferably with its opening pushed over an axis, e.g., an auxiliary tube, which runs through the housing positioned in the machine. Further, the cut end of the retainer is positioned on one end of the preparation, which is later pulled out of the capsule. In a ninth step, the retainer is bonded to the one end of the preparation, in a clamp bonding area. The retainer can be wound around the holder by rotating the holder around a winding axis as described, or alternatively, the retainer can be rotated around the fixed holder to wind the retainer.

In a preferred embodiment of the applicator, the cap of the applicator that covers the opening of the applicator and that is removed prior to use to allow the dosage form to exit the body of the applicator includes a lid and a plurality of springs configured to press a support element onto the capsule, which preferably touches the one end of the capsule positioned inside the holder that preferably faces towards the cap. For example, the cap is similar to a cap for effervescent tablets. Therefore, in a preferred embodiment the capsule is vertically positioned inside the holder and the support element presses onto the one end of the capsule pointing towards the lid. The lid preferably further comprises a drying agent, to prevent moisture from rendering the dosage form unusable, e.g., during storage. The plurality of springs can be made of plastic or of any elastic material, such that a pressure force is exerted by the springs onto the support element, which then mechanically fixes the capsule in the holder by pushing the support element towards the capsule's surface. The support element preferably has a shape complementary to the contour of the capsule, so that the capsule contour fits into the support element.

In a preferred embodiment, the pharmaceutical dosage form comprises the capsule device, which contains the pharmaceutical preparation for the application to a mucous membrane, preferably to the esophageal mucosa, and a sinker, wherein the preparation is connected to the retainer of an applicator configured to withdraw the preparation upon swallowing of the dosage form, wherein the retainer then dissolves after a period of time in the mouth and wherein the preparation sticks to, in particular the esophageal, mucous membrane wherein the sinker and the capsule device dissolve in the stomach.

In a preferred embodiment the pharmaceutical dosage form is produced, connected to the retainer and packed into the applicator according to the following process steps:

In a first step, the capsule device is inserted into a machine by an inserting case. The capsule device comprises the first and the second halve-capsule shell joined by overlapping of the first halve-capsule shell and the second halve-capsule shell in a joined position, is.

In a second step, the second halve-capsule shell is gripped by the inserting case and separated from the first halve capsule shell. Additionally, the applicator housing is positioned on the machine.

In a third step, the first halve capsule shell is moved by a piston in the direction of a punching tool so that an insertion pin of the punching tool enters the cavity, in particular the cylindrical cavity, of the first halve capsule shell. The insertion pin thereby holds the first halve capsule shell so that a part of the punching tool that moves laterally with respect to the direction of movement of the insertion pin, punches an opening and/or a recess out of the wall of the first halve capsule shell.

In a fourth step, the insertion pin is pulled out of the cavity of the first halve capsule shell. The first halve capsule shell is positioned so that the punched opening points preferably in the direction of the applicator housing. The punching tool uses a negative pressure to transport the material punched out of the capsule wall away from the first halve capsule shell.

In a fifth step, the preparation is clamped between two holding jaws and slightly stretched by increasing the distance between the two clamping jaws. On one side of one of the two holding jaws, the preparation, which runs beyond this holding jaw, is cut off flush with the holding jaw, thereby producing a cut end of the preparation, while the preparation is still stretched. This cut end of the preparation serves as a starting point for winding the preparation. Therefore, a winding mandrel is threaded onto the stretched preparation between the two jaws. Since now the end part of the preparation is also held by the winding mandrel, the one of the holding jaws used for cutting is opened. After or during opening of said jaw, the winding mandrel rotates so that the cut end of the preparation, which has been previously clamped in said holding jaw is wound onto the winding mandrel, thereby producing a first winding.

In a sixth step, the other of the two holding jaws is opened, and the winding mandrel rotates. In this process, the further preparation is wound onto the rotating winding mandrel. Once a predetermined length of the preparation has been wound up, the rotary movement of the winding mandrel is stopped. The length is determined preferably such that an end section of the preparation is not wound, i.e., the preparation is not fully coiled. Said end section of the preparation is used to connect the preparation with the retainer, i.e., with an end section of the retainer.

In a seventh step, the preparation wound onto the winding mandrel is positioned in front of the punched opening of the first halve-capsule shell. The wound preparation can also partially protrude into the punched opening or recess. The unwound end section of the preparation remains outside the first halve capsule shell.

In an eighth step, the winding mandrel is pulled out of the coiled preparation and the coiled preparation is positioned inside the first halve capsule shell through the opening of the first halve capsule shell by mechanically pushing the coiled preparation through the opening into the first halve capsule shell.

In a ninth step, an insertion pin moves into the particularly hollow cylindrical opening of the first halve capsule shell, whereby the coiled preparation positioned inside the first halve capsule shell in step eight is positioned deeper into the first halve capsule shell. The end section of the preparation, which is not coiled, is positioned on a bonding area of the machine.

In a tenth step the retainer is configured to be wound around the holder of the applicator. Step ten can also take place simultaneously or earlier or later to other production steps. To wind the retainer around the holder, the retainer is mechanically fixed in the machine by a clamp and cut unit. The clamp and cut unit comprises clamping jaws in between which the retainer can be clamped to tension the retainer. The clamp and cut unit further comprises a cutter to cut the retainer and a guiding block to ensure a smooth cut of the retainer. In the tenth step, the retainer is tensed by moving the clamping jaws.

In an eleventh step the holder is positioned on a winding unit and is placed along the tensed retainer and the retainer is attached to the wall structure of the holder. Since the retainer is attached to the holder, the retainer is wound onto the holder when the holder is rotated.

In a twelfth step one of the clamping jaws of the clamp and cut unit is opened, so that the retainer can slide through the clamping jaw in a guided manner for winding. The other clamping jaw of said unit, which further comprises the cutter, remains closed.

In a thirteenth step, the winding unit begins to rotate, e.g., by rotating a clutch that fixes and supports the holder, thereby wrapping the retainer around the holder. Ideally, the rotational movement is superimposed by a vertical translational movement, such that the retainer is wound onto the holder in juxtaposed positions.

In a fourteenth step, after a predetermined length of the retainer is wound around the holder, a clamping jaw of the winding unit further clamps the retainer, such that when the cutter of the still closed clamping jaw of the clamp and cut unit cuts the retainer, the retainer remains clamped by the clamping jaw of the winding unit instead. The cutter then cuts the retainer. The retainer is however not cut directly at the clamping jaw of the winding unit, but further away from said unit. Thereby, a short section of the retainer remains left after cutting, outside of the clamping jaw of the winding unit. This short section of the retainer is used to connect the retainer to the preparation in the further processing steps. The winding unit further comprises a robot gripper.

In a fifteenth step, the robot gripper of the winding unit transports the holder with the retainer wound around the holder and the retainer being clamped at one end by the clamping jaw of the winding unit, to the machine part where the first halve capsule shell is positioned and where the housing of the applicator is placed. The robot gripper positions the holder on an axis by pushing the holder into the axis, which is located inside the housing. In doing so, the holder is only pushed onto the axis to the extent that the short section of the retainer, used for connecting the retainer to the preparation, can be positioned onto a bonding area, which is located outside the housing. The bonding area further comprises the end section of the preparation, which extends through the opening of the first halve capsule shell, i.e., which extends through the aperture of the capsule device when both halve shells are joined in the joining position and which is not coiled.

In a sixteenth step, the retainer and/or the preparation are moistened preferably by an atomizer nozzle. Humidification takes place in the bonding area.

In a seventeenth step, the retainer is pressed onto the preparation by a stamp in order to connect the preparation to the retainer. The connection is such that a tensile force can be transmitted between the retainer and the preparation.

In an eighteenth step, the sinker is produced and inserted into the second halve capsule shell. Step eighteen can also take place simultaneously or earlier or later to other production steps. The sinker is pressed from a powder preferably by use of pressing pins. A robotic rotary arm can move into the powder, suck in a predetermined amount of powder and press the powder. The robotic rotary arm then moves out of the powder and rotates over the second halve capsule shell where the pressed powder is preferably directly inserted as a sinker into the second halve capsule shell. The step of producing the sinker can be made independently of the other processing steps. I.e., the sinker can be produced in advance or in parallel to the further processing steps and the robotic arm may only grip a ready pressed or otherwise manufactured sinker. It is also possible that no sinker is present in the capsule device, so that the eighteenth process step can also be omitted.

In a nineteenth step, the second halve capsule shell, with and/or without the sinker, is positioned above the first halve capsule shell by means of the inserting case. After the capsule halves are positioned on top of each other, the second halve capsule shell is pressed over the first or into the first halve capsule shell through the inserting case, so that the pharmaceutical dosage form is obtained with the second halve-capsule shell having a wall overlapping a cross-section of the opening thereby forming the aperture of the capsule device in the joined position. Thereby, the end section of the preparation, which is uncoiled, extends out of the aperture and onto the bonding area and is connected to the end section of the retainer.

In a twentieth step, the capsule device of the pharmaceutical dosage form is gripped with a gripping tool and positioned over the holder and then placed in the holder.

In a twenty-first step, the housing is pushed towards the holder and over the holder. An end cap is positioned on the housing. This closes the housing, which now contains the retainer wound onto the holder, and the pharmaceutical dosage form placed in the holder, whereas the end section of the retainer is connected to the end section of the preparation, such that the retainer pulls the preparation out of the capsule device, when the retainer is fully unwound, e.g., if the patient swallows the dosage form.

Further preferred embodiments of the method of producing the pharmaceutical dosage form according to the invention and further preferred embodiments of the method of producing a capsule device for a pharmaceutical dosage form according to the invention may be taken from the description according to the invention and its embodiments, as well as from the description of the embodiments according to the figures.

BRIEF DESCRIPTION OF THE DRAWINGS

Exemplary embodiments of the present invention will be described in greater detail below with reference to the accompanying drawings and samples, from which further features, advantages, and embodiments can be learned.

FIG. 1a shows a schematic side view of a dosage form according to a first embodiment of the invention.

FIG. 1b shows a detail of the area marked by "X" in FIG. 1a.

FIG. 1c shows an alternative configuration of the area marked by "X" in FIG. 1a.

FIG. 2a shows a top view on a first and a second halve-capsule shell, aligned to each other for forming a capsule device for a pharmaceutical dosage form according to another preferred embodiment of the invention.

FIG. 2b shows a top view on a first and a second halve-capsule shell, aligned to each other for forming a capsule device for a pharmaceutical dosage form according to another preferred embodiment of the invention.

FIG. 2c shows a top view on the first and the second halve-capsule shells of FIG. 2a, being sticked together along the direction of movement M.

FIG. 2d shows a top view on the capsule device formed by the joined position of the first and the second halve-capsule shells of FIG. 2a.

FIG. 2e corresponds to FIG. 2d, wherein the second halve-capsule shell is shown transparent for marking the area of the wall of the second halve-capsule shell overlapping the opening, thereby forming the aperture.

FIG. 3a is a side view of the situation in FIG. 2a.

FIG. 3b shows a pharmaceutical preparation in its compact form being inserted through the opening of the first halve-capsule device, forming an exemplary step of the method according to the invention of producing the pharmaceutical dosage form.

FIG. 3c shows a pharmaceutical preparation in its compact form being inserted inside the hollow space of the first halve-capsule device, forming another exemplary step of the method according to the invention of producing the pharmaceutical dosage form.

FIG. 3d shows a pharmaceutical dosage form, according to an embodiment of the invention, using the capsule device of FIG. 2d.

FIG. 3e shows the pharmaceutical dosage form of FIG. 3d, wherein the second halve-capsule shell is shown transparent.

FIG. 4a shows a first and a second halve-capsule shell for a pharmaceutical preparation, and also shows an axle X of rotation being located within the opening and having a strip-like preparation connected to the axle, forming an exemplary step of the method according to the invention of producing the pharmaceutical dosage form.

FIG. 4b shows the first and the second halve-capsule shell for a pharmaceutical preparation according to FIG. 3d, including an axle X of rotation being located within the opening and having a strip-like preparation partly wound around the axle by rotation (R), forming an exemplary step of the method according to the invention of producing the pharmaceutical dosage form.

FIG. 4c shows the first and the second halve-capsule shell for a pharmaceutical preparation according to FIG. 3d, including an axle X of rotation being located within the opening and having a strip-like preparation completely wound around the axle by rotation (R), forming an exemplary step of the method according to the invention of producing the pharmaceutical dosage form.

FIG. 4d shows the second halve-capsule shell for a pharmaceutical preparation according to FIG. 3d, including a sinker element being inserted into the hollow space of the second halve-capsule shell, forming an exemplary step of the method according to the invention of producing the pharmaceutical dosage form.

FIG. 5a illustrates a first step of using the kit to facilitate administering the pharmaceutical dosage form before swallowing of the dosage form by the patient.

FIG. 5b illustrates a second step of using the kit to facilitate administering the pharmaceutical dosage form after swallowing of the dosage form by the patient.

FIG. 6c relates to the kit and illustrates the steps of the method of connecting the retainer to the holder of the preparation.

FIG. 6d relates to the kit and illustrates the steps of the method of joining of the first halve-capsule shell with the second halve-capsule shell, while the retainer is connected to the preparation.

FIG. 6e relates to the kit and illustrates the steps of the method of assembling of the capsule device with the applicator, while the retainer is connected to the preparation.

FIG. 1a shows the capsule device 1 for the application to a mucous membrane, comprising a preparation 2 having an elongated shape and comprising the active pharmaceutical ingredient. The preparation 2 is shown in a compact condition: assuming that the preparation has a strip-like shape, FIG. 1a shows a side view of the strip-like preparation being wound as a spiral around a virtual axis, which is perpendicular to the drawing sheet. In an expanded condition, when the preparation is pulled out from the slit-like aperture 5 of the capsule 3, the strip-like preparation will have an elongated shape of a substantially straight strip.

Figures 6A, 6B:
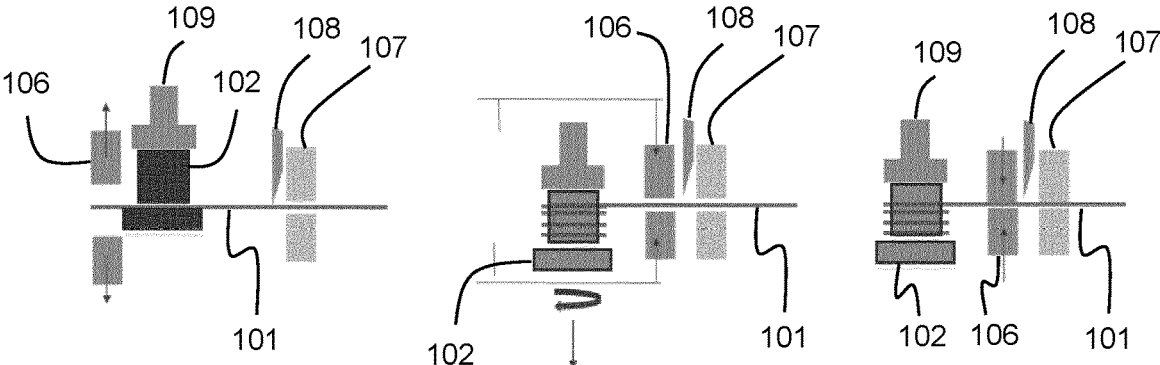
FIG. 6a relates to the kit and illustrates the steps of the method of attaching the retainer to wall structure of the holder.
FIG. 6b relates to the kit and illustrates the steps of the method of winding the retainer around the holder of the applicator, after the retainer is attached to the wall structure of the holder.

The capsule device 3 has the shape of a capsule and comprises a hollow space 4, which accommodates the preparation 2 being in the compact condition. The capsule consists of a thin wall having a thickness of about 50 μm to 200 μm, made from a biodegradable or non-biodegradable material.

The capsule device has an aperture 5, formed as a planar curved slit.

The width a of the aperture 5 formed as a curved slit is defined by measuring the distance of opposing surfaces 5a of the capsule wall of the first halve-capsule shell 3a and the second halve-capsule shell 3b in a direction parallel to the length axis A. The distance 'a' may be a constant value between 200 μm and 600 μm, for example. The thickness t of the preparation may be a constant value between 20 μm and 150 μm, for example.

Regarding the outer dimensions of a capsule device, for example, the height H of the capsule 3 may be 8 mm, the width W of the capsule may be 4 mm. However, other dimensions of a capsule device are generally possible considering the desired administration site of a patient.

A first end 2a of the preparation 2 extends, in the compact condition of the preparation, through the aperture 5 for allowing grabbing and pulling out the preparation from the hollow space into the surrounding area of the capsule device, thereby transferring the preparation 2 from the compact condition to the expanded condition. Pulling out the preparation, i.e. the pull-out movement P (cf. FIG. 1b), may be the result of fixating and end 2a of the preparation 2 and pulling the capsule device in a direction M opposite to P. This is the case for example, by using the process of administering the capsule device by swallowing the same and connecting the end 2a of the preparation to a retainer of an applicator comprising a drinking cup as it is shown in FIGS. 5a, 5b.

The first end 2a may have an end portion (cf. FIG. 1c), which has a shape different from the strip 2. For example, the end portion may form a sealing part suitable to be arranged at the aperture 5 for sealing the aperture 5, before the end portion is pulled out from the aperture. The end portion may further be configured to connect to the retainer of the applicator by providing a bonding area.

FIG. 1b shows a zoomed view of the aperture area 5. The aperture 5 results from the second halve-capsule shell 3b, as shown in FIG. 1b, c, being telescoped over the first halve-capsule shell 3a, thereby overlapping the opening 6 of the first halve-capsule shell to form the slit like aperture 5. The slit-like aperture 5 and the strip-like preparation 2 are dimensioned such that, when the preparation is pulled out from the aperture, a spacing (S1; S2) is provided measured in the aperture cross section CS of the aperture 5 between the preparation 2 and a surface 5a of the capsule device defining the aperture 5. Here, the central length axis A of the capsule runs parallel to the aperture cross section CS. The capsule device 3 as shown in FIG. 1a comprises a first halve-capsule shell 3a and a second half-capsule shell 3b, wherein when the first half-capsule shell 3a and the second half-capsule shell 3b are telescoped into each other to form the capsule device 3, the opening 6 of the first halve-capsule shell 3a is partially covered by the second half-shell 3b to form the slit like aperture 5. Such an opening 6 may be produced by milling out the capsule material using a plate-shaped milling tool, for example a plate shaped saw blade. The overlapping position, i.e., the joined position between the two halve-capsule shells 3a, 3b is indicated in FIG. 1a by a dotted line marked with B.

As shown in FIG. 1b, the thickness t of the strip 2 is remarkably smaller than the width a of the planar curved slit 5. For example, the thickness t may be a constant value between 20 μm and 150 μm. The spacing S=S1=S2 is measured by positioning the preparation 2 in the center of the aperture 5 and in a centered-and-aligned position of the strip surfaces being in parallel to and facing the surfaces 5a of the capsule. The spacing S is present and may be—in average—substantially constant while the preparation 2 is pulled out from the aperture, which means, substantially along the whole length of the elongated preparation. However, the scope of the invention also may cover embodiments of dosage forms, where the spacing between the preparation and the surfaces 5a, which define the aperture, varies—due to a varying thickness t of the preparation 2—, or where the spacing is partly interrupted—due to a portion-wise variation of dimensions a and t, including the portion-wise dimensioning of a=t.

In cases, where the preparation has a string-like shape, the dimensions may be measured in analogy, and in case of irregularly shaped preparation, the dimensions may be determined by averaging.

As shown in FIG. 1c, the first end 2a may have an end portion forming an enlarged part, which may be configured for avoiding that the preparation is lost inside the capsule 3, which would make it different for a patient or applicant to recover the end 2a for pulling out the strip and applying the dosage form in the predetermined way. The end portion 2a may also be configured to be arranged at the aperture 5 for sealing the aperture 5, before the end portion 2a is pulled out from the aperture. A portion 7 may be provided at the end part, being configured to connect a line, e.g. a retainer from an applicator, to the end part 2a. The width a' of the aperture 5 in the direction, which runs perpendicular to the axis A indicating the elongated shape of the capsule 3, is measured between the opposing surface 5a' of the second halve-capsule shell. The width a' can be dimensioned similar to the width of the preparation end part 2a.

FIG. 2a shows a top view on a first 11 and a second 12 halve-capsule shell, aligned to each other for forming a capsule device 13 for a pharmaceutical dosage form 10 according to another preferred embodiment of the invention. The first halve-capsule shell 11 has a first end closed by a spheroid cap 11a, and has a second end, which is a hollow-cylindrical wall 11b providing an opening of the first halve-capsule shell 11. The second halve-capsule shell 12 has a first end closed by a spheroid cap 12a, and has a second end, which is a hollow-cylindrical wall 12b providing an opening of the second halve-capsule shell 12. The first halve-capsule shell 11 has a hollow-cylindrically shaped wall 11c completely surrounding the opening 16, which basically is a hole in the wall 11c. Stability is provided by the wall frame 11c around the opening 16.

FIG. 2b shows a top view on a first 11' and a second 12' halve-capsule shell, aligned to each other for forming a capsule device for a pharmaceutical dosage form according to another preferred embodiment of the invention. The first halve-capsule shell 11' has a first end closed by a spheroid cap 11a', and has a second end, which is a hollow-cylindrical wall 11b' providing an opening of the first halve-capsule shell 11'. The second halve-capsule shell 12' has a first end closed by a spheroid cap 12a', and has a second end, which is a hollow-cylindrical wall 12b' providing an opening of the second halve-capsule shell 12'. The hollow-cylindrical wall section 11c' does not fully surround the opening 16, in particular the recess 16', which extends from the wall border of the second end 11b' towards the first end 11a'. The recess offers enough space for handling the preparation, in particular for inserting the preparation 2 in its compact shape either along a direction perpendicular to the plane of the drawing, and/or along the direction M, inside the hollow space of the first halve-capsule shell 11'.

FIG. 2c shows a top view on the first and the second halve-capsule shells of FIG. 2a, being sticked together by a sliding movement along the direction of movement M. The cylindrical part of the second halve-capsule shell 12 may have a slightly larger diameter than the cylindrical part of the first halve-capsule shell 11, for facilitating the engagement of the first 11 and a second 12 halve-capsule shells.

FIG. 2d shows a top view on the capsule device 13 formed by the joined position of the first and 11 the second 12 halve-capsule shells of FIG. 2a. The aperture 15 is a slit extending circumferentially and tangentially around the axis a within the capsule wall. The cross-section A_o of the aperture is remarkably smaller than the cross-section A_a of the opening 16, e.g. by a factor f=0.05 to 0.2: A_o=f*A_a. This way, the preparation, which was easily to be inserted through the opening 16 in the disassembled position of the first 11 and a second 12 halve-capsule shells, cannot fall out through the aperture 15 in its compact condition but may be easily pulled out through the aperture 15 in its elongated position when unwinding from the wound condition during swallowing (see FIG. 9b).

FIG. 2e corresponds to FIG. 2d, wherein the second halve-capsule shell is shown transparent for marking the area 12c of the wall 12b of the second halve-capsule shell overlapping the opening 16, thereby forming the aperture 15.

FIG. 3a is a side view of the situation in FIG. 2a. The opening 16 has a rectangular shape, when projected onto a plane, but follows the cylindrical shape of the wall 11b, in a circumferential direction. It basically opens the cylinder along almost its full width W (cf. FIG. 1b), allowing the preparation in its compact condition to be inserted through the opening 16 into the hollow space 14 of the capsule device or of the first halve-capsule shell, respectively, along a direction N being perpendicular to the axis A (cf. FIG. 3b).

FIG. 3b shows a pharmaceutical preparation in its compact form being inserted through the opening 16 of the first halve-capsule shell 11.

FIG. 3c shows a pharmaceutical preparation in its compact form being fully inserted inside the hollow space 14 of the first halve-capsule shell 11, while an end 2a of the preparation in its compact shape extends through the opening 16, even while the second halve-capsule shell 12 is moved to engage with the first halve-capsule shell 11, thereby continuously reducing the free cross section of the opening 16, until the joined position in FIG. 3d is reached, which shows the completed pharmaceutical dosage form 10.

FIG. 3d shows the pharmaceutical dosage form 10, using the capsule device of FIG. 2d. FIG. 3e shows the pharmaceutical dosage form 10, wherein the second halve-capsule shell 12 is shown transparent to show the position of the preparation in its compact condition inside the hollow space 14.

Figures 4A, 4B, 4C, 4D:
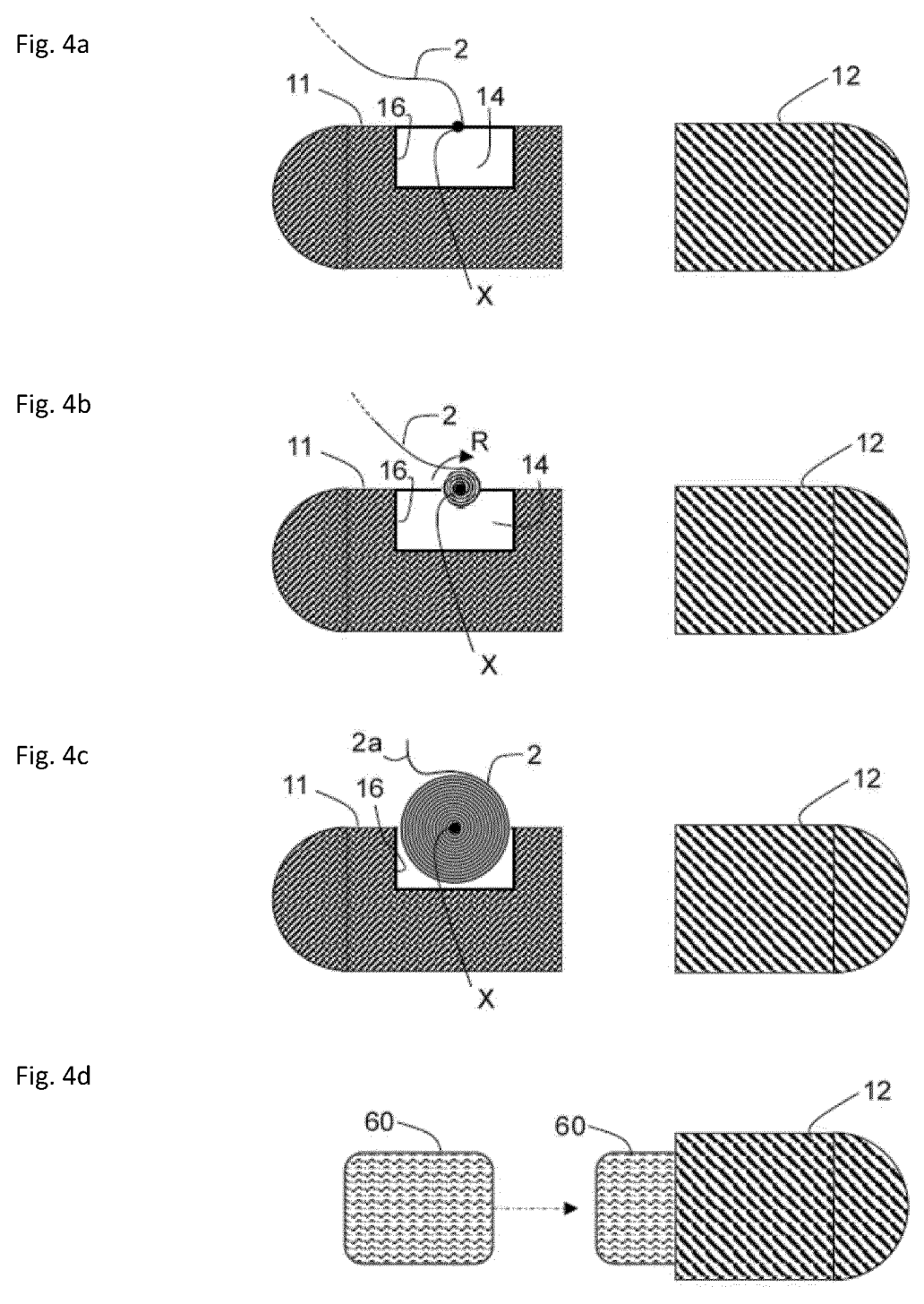

FIG. 4a shows a first 11 and a second 12 halve-capsule shell for a pharmaceutical preparation and shows an axle X of rotation being located within the opening 16 and having a strip-like preparation 2 connected to the axle X, forming an exemplary step of the method according to the invention of producing the capsule device and assembling for a pharmaceutical dosage form.

FIG. 4b shows the first 11 and the second 12 halve-capsule shell for a pharmaceutical preparation according to FIG. 3d, including an axle X of rotation R, the axle being located within the opening—or in front thereof—and having a strip-like preparation 2 partly wound around the axle by rotation (R), forming an exemplary step of the method according to the invention of producing the capsule device and assembling for a pharmaceutical dosage form. The direction of rotation (R) in FIG. 4b is selected as an example and can therefore also be in the opposite direction to the direction of rotation (R) shown.

FIG. 4c shows the first 11 and the second 12 halve-capsule shell for a pharmaceutical preparation according to FIG. 3d, including an axle X of rotation being located within the opening and having a strip-like preparation completely wound around the axle by rotation (R), forming an exemplary step of the method according to the invention of producing the capsule device and assembling for a pharmaceutical dosage form.

FIG. 4d shows the second halve-capsule shell for a pharmaceutical preparation according to FIG. 3d, including a sinker element 60 being inserted into the hollow space of the second halve-capsule shell 12, forming an exemplary step of the method according to the invention of producing the capsule device and assembling for a pharmaceutical dosage form.

FIG. 5a shows the administration of a pharmaceutical dosage form comprising the capsule device as herein described by a patient. A drinking cup 901 is filled with a liquid and an applicator 902 is attached to the cup 901. The applicator 902 comprises a pharmaceutical dosage form comprising the capsule device 903 and a retainer 904, which is connected to the preparation, included into the capsule device 903.

FIG. 5b illustrates the procedure when the patient swallows the capsule device 903 and it is transported through the esophagus towards the stomach. The retainer 904 pulls the preparation 905 out of the capsular device 903. The preparation 905 then spreads along the esophagus so that the active ingredient of the preparation 905 is delivered to the mucosa of the esophagus.

FIG. 6a relates to the method of winding the retainer 101 around the holder 102 of the applicator 103 by machine 100. Therefore, as shown in FIG. 6a, in a first step for wrapping the retainer 101 around the holder 102, the retainer 101 is mechanically fixed in a machine 100, comprising a clamp and cut unit 110. The cut unit 110 comprises clamping jaws 106, a cutter 108 and guiding means 107. In a second step the retainer 101 is tensed by moving the clamping jaws 106. In a third step the holder 102 is positioned along the tensed retainer 101 means a mechanical clutch 109 and the retainer 101 is clamped in a groove of the wall structure of the holder 102.

FIG. 6b relates to the method of winding the retainer around the holder of the applicator, after the retainer is attached to the wall structure of the holder. In a first step, as shown in FIG. 6b, the jaws 106 for clamping the retainer 101 are opened. In a second step, the holder 102 is rotated in a winding unit, e.g. by rotating the clutch 109 that fixes and supports the holder 102, thereby wrapping the retainer 101 around the holder 102. The rotational movement is superimposed by a vertical translational movement, such that the retainer 101 is wound onto the holder 102 in juxtaposed positions, whereas after the retainer is sufficiently wound around the holder 102, the clamping jaws fix the retainer 101 in a sixth step again.

In a third step, the knife-like component 108 of the machine 100 cuts through the one end of the retainer 101, which is connected to the preparation 104 in the further following steps.

FIG. 6c relates to the method of connecting the retainer to the holder of the preparation means joining the retainer 101 with the preparation 104, while further assembling the kit by machine. In a first step, the positioning of the holder 102 with the retainer 101 wrapped around it over the opening 110 of the applicator housing 111 is done, in particular, by machine. Therefore, the holder 102 is with its opening 110 pushed over an axis 112, e.g., an auxiliary tube. The axis 112 thereby runs through the housing 111, which is already positioned in the machine 100. Further positioned in the machine 100 and arranged next to the applicator housing 111, is the first halve-capsule shell 105a of the capsule device 105, such that the preparation 104 extends at least partially out of the first halve 105a onto a bonding area 113 of the machine 100. Further arranged within the bonding area 113 of the machine 100 is the cut end 101a of the retainer 101. The cut end 101a later pulls the preparation 104 out of the capsule device 103.

FIG. 6d relates to the method of joining of the first halve-capsule shell with the second halve-capsule shell, while the retainer is connected to the preparation. As shown in a first step, the retainer end part 101a is bonded to the one end of the preparation 104, in the clamp bonding area 113. Thereby a support 114 moves down towards the bonding area 113 and presses onto the preparation 104 and the retainer end part 101a overlapping each other. Bonding is further described in FIG. 10. In a second step, the second halve-capsule shell 105b is positioned above the first halve 105a together with sinker elements 115. In a third machine step, the two halves 105a, 105b are telescoped or joined or slid into each other, such that the opening is partially closed to form the aperture of the capsule device 105, whereas the end part of the preparation 104 can be withdrawn by the now finally connected or joined retainer 101 through the aperture.

FIG. 6e relates to the method of assembling of the capsule device with the applicator, while the retainer is connected to the preparation. Therefore, FIG. 6e shows the steps of assembling the pharmaceutical dosage form, i.e., the capsule device 105, comprising the preparation 104 and in the case shown, the sinker elements 115, with the applicator 103. Therefore, in a first step, a gripping element 116, which holds the capsule device 103 e.g., by negative pressure, is positioned above the capsule device 103 to grip the device 103 and to transport the capsule device 103 above the housing 111 of the applicator 105. In a second step, the capsule device 103 is deposited inside the housing 111. The housing 111 additionally contains the retainer 101 wound around the holder 102 and positioned inside the opening 110 of the housing 111 as described in the earlier steps with respect to FIGS. 6c and 6d. In a third step, the housing 111 of the applicator 105 is closed by an end cap 117.

Figure 7:
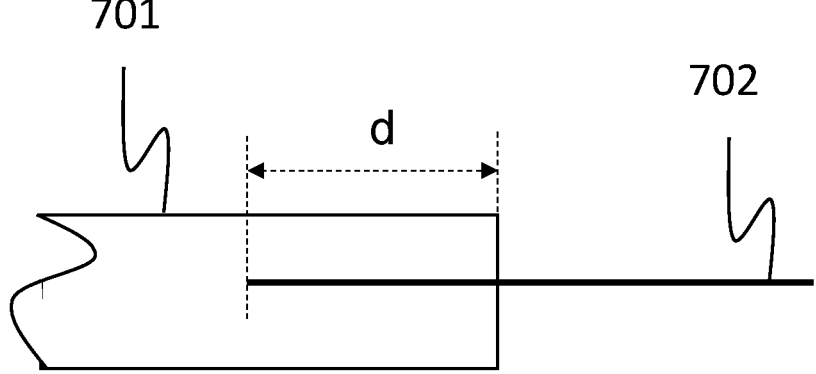
FIG. 7 illustrates the end part of the preparation being connected to the retainer of the applicator.

FIG. 7 shows the end part of the preparation 701 being connected to the retainer 702, e.g. an end part of the retainer, of the applicator. To connect the retainer 702 with the end part of the preparation 701, in a first step the retainer is immersed into an aqua pure solution. In this embodiment, water acts as an adhesive. However, other embodiments are also conceivable in which substances other than water can be used as adhesives.

The retainer is preferably immersed into the solution for a period of 1 to 10 seconds, or 1 to 5 seconds or for about 1 second. In a second step, the immersed retainer 702 is positioned on the end part 701 which is wetted with water. Thereby the retainer 702 overlaps the end part of the preparation 701 over an overlap distance d, which ranges from 0.5 to 2 cm, or 0.5 to 1.5 cm or 0.5 to 1 cm or preferably is 1 cm. After positioning of the retainer 702, the retainer 702 is pressed onto the end part of the preparation 701, whereas the end part 701 is still wet with water. Pressing occurs over a period of time of preferably 1 to 10 seconds, or 1 to 5 seconds or 2 to 3 seconds. Pressing is made by use of a contact pressure stamp. In a further third step, the joined retainer 702—preparation 701 is dried before further steps of processing the joined pieces for a period of 1 to 10 minutes or 2 to 8 minutes or preferably for 5 minutes. Alternatively, the retainer 702 is not immersed but positioned dry on the end part 701, such that the retainer 702 overlaps the end part of the preparation 701 over the overlap distance d, and the retainer together with the end part 701 is sprayed with aqua pure before pressing. Spraying can be carried out with the aid of a nozzle, e.g., a spray nozzle or an atomizer nozzle, to atomize the liquid onto the surface to be sprayed. Use of a nozzle facilitates dispersion of the liquid into a spray. Thereby the nozzle distributes the liquid over the area, which comprises at least the overlapping distance d, increases the liquid surface area, and creates an impact force on a solid surface.

Figure 8:
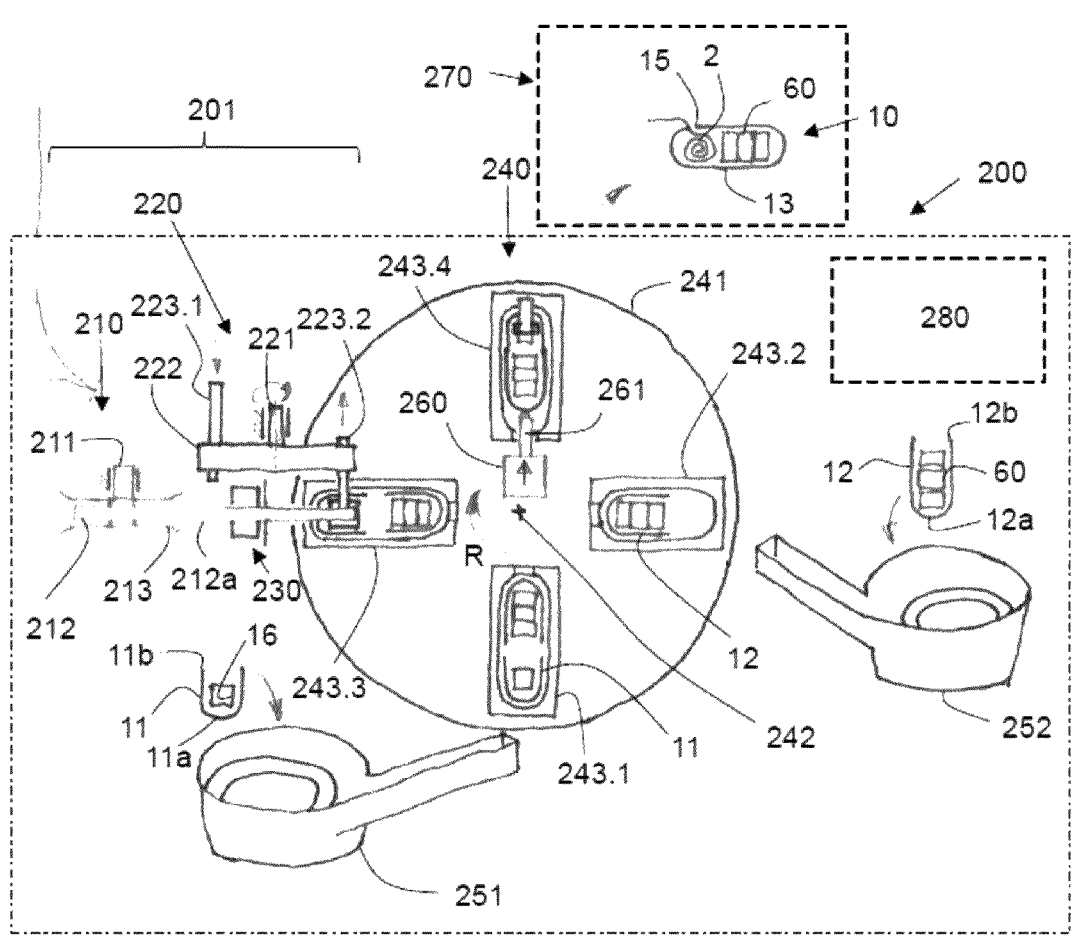
FIG. 8 exemplarily shows a production machine according to the invention for producing the pharmaceutical dosage form according to the invention, in particular by executing the method according to the invention.

FIG. 8 exemplarily shows a production machine according to the invention for producing the pharmaceutical dosage form according to the invention, in particular by executing the method according to the invention. The production machine 200 is configured for producing the pharmaceutical dosage form according to the invention, in particular by executing the method according to the invention, the production machine comprising a positioning device 240 for positioning the first halve-capsule shell in a mounting position. A connection device 260 having a movable element 261 configured for connecting the second halve-capsule shell and the first halve-capsule shell to a joined position by moving the first 11; 11' and second 12; 12' halve-capsule shells towards each other, such that a wall 12c of the second halve-capsule shell overlaps a cross-section of the opening 16; 16' by an amount controlled by the movement of the movable element 261 thereby forming the aperture 5; 15 of the capsule device 3; 13 in the joined position.

The positioning device 240 comprises four holding members 243.1; 243.2; 243.3; 243.4 for holding one or more of the first halve-capsule shell and/or the second halve-capsule shell in place. The holding member provides a retaining space, which is shaped to retain the first halve-capsule shell and/or the second halve-capsule shell by a positive fit connection. The positioning device 240 the holding members, may be configured to hold a plurality of first and/or second halve-capsule shells in place in parallel, while here only one capsule is generated at each mounting position. This way, the throughput of the production method can be increased. The positioning device 240 provides for positioning four of the first halve-capsule shells and four of the second halve-capsule shells in four mounting positions, each provided by a holding member 243.1; 243.2; 243.3; 243.4. Thereby, several steps of the production of a pharmaceutical dosage form can be performed in parallel using the plurality of mounting positions, in particular working stations defined by the holding members.

Figure 11:
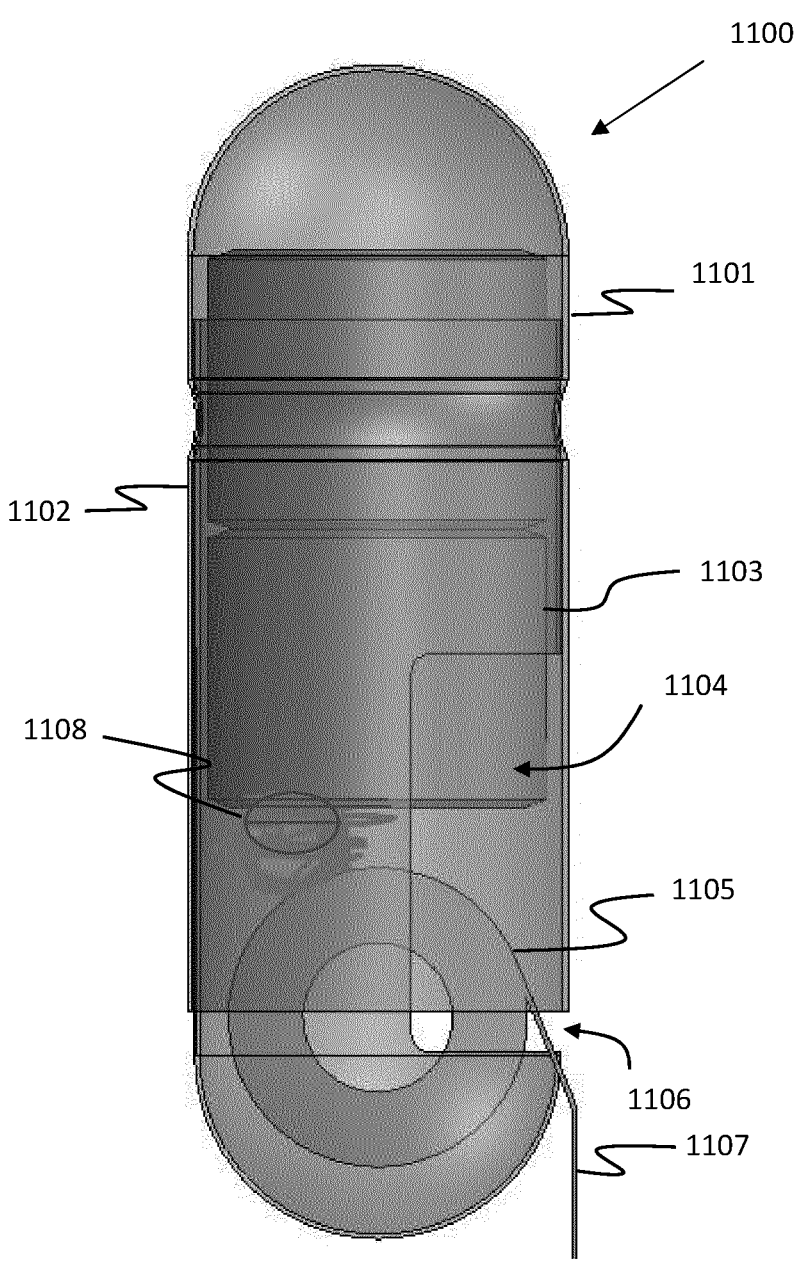
FIG. 11 shows a schematic side view of a pharmaceutical dosage form according to a further embodiment of the invention.

The positioning device 240 comprises a rotatable platform 241 carrying the workings station. Each working station comprises one holding member being located along a radially outer area of the rotating platform. The movable platform 241 is arranged rotatably at a base member (not shown) for rotating around an axis 242, configured for rotating each working station to a working position of the production machine. At a first working position (where the holding member 243.1 is shown in FIG. 11), a feeding device 251 for feeding at least one first halve-capsule shell 11; 11' to the mounting position provided by the holding member 243.1 is arranged. At a second working position (where the holding member 243.2 is shown in FIG. 11), a feeding device 252 for feeding a second halve-capsule shell 12; 12' to a mounting position provided by the holding member 243.2 is arranged.

At a third working position (where the holding member 243.3 is shown in FIG. 8), an equipment device 201 may be arranged for equipping a first halve-capsule shell 11; 11' with a preparation 2, preferably in its compact condition, the equipment device 201 comprising a transport device 220 for transporting an end 212a; 2a of a preparation to the mounting position, and comprising a compacting device 223.1; 223.2, in particular a winding device, for transferring the preparation 212; 2 from an elongated condition to a compact condition, in particular a folded or wound condition.

At a fourth working position (where the holding member 243.4 is shown in FIG. 8), a reception station 270 may be provided for receiving the readily produced pharmaceutical dosage forms 10, and possibly forwarding the same to a storage or a conveyor system (not shown).

The production machine, in each case, preferably comprises an electronic control device 280 for controlling each action, which is automatically performed by the production machine, in particular by controlling the activity and parameters of at least one drive driving the rotation of the positioning device around axis 242, the feeding of capsule parts by devices 252 and 251, the transport of a preparation by the transport device, the motion of a compacting device, in particular the rotation of a winding device, the cutting motion of a cutting device, the actuation motion of an actuation device, the connection motion of a connecting device 260, and any further device. The electronic control device 280 may comprise a user interface for allowing a user controlling the production machine, and/or a control software for controlling the production machine, in particular a computer program programmed to implement each step of the method according to the inventions including all possible and preferred steps described herein.

The production machine comprises a preparation storage device 210, which provides a storage roll 212 of a preparation, which can be released from the roll by rotation of the roll 212 around axis 211, thereby letting the elongated preparation move along a direction towards the cutting device 230 and towards the holding member 243.3, which provides the working position the movement of the elongated preparation 212 is guided by a guiding unit 213 also including the roll 214. A position 212a of the preparation 212 (afterwards forming the first end 2a of the elongated preparation 2) is gripped by the rotating axle 223.1, which is moved by rotation of the rotating disk 222 around axis R1 to the mounting position at the holding member 243.3. See FIG. 9a.

Figure 9A:
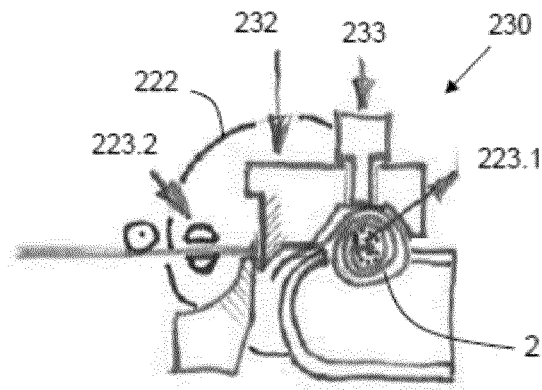
FIG. 9a exemplarily shows an equipment device of a production machine, for equipping the first halve-capsule shell with a preparation, in a first step, wherein the elongated preparation is wound up at a mounting position.

FIG. 9a exemplarily shows an equipment device 201 of a production machine 200, for equipping the first halve-capsule shell 11; 11' with a preparation 2, in a first step, wherein the elongated preparation 212 is wound up at a mounting position at the holding member 243.3.

The production machine 200 comprises the transport device 220 for transporting an end of a preparation 212a, which has an elongated shape and comprises an active pharmaceutical ingredient, from a storage position of the preparation to a mounting position, where the preparation is positioned to be inserted into the hollow space 14 of the first halve-capsule shell 11; 11', which is in the mounting position 243.3, in particular to be inserted through the opening 16. Here, the transport device has a rotatable transport member 222, which is configured to receive at least a part 212a of a preparation 212 at a first position at 223.2, in particular after being released form a preparation storage device 210, and to transport said at least part of the preparation 212a to the mounting position 243.3 by rotation R1. The movement or rotation of the transport device 222 may be controlled by an electronic control device 280 of the production machine 200.

The rotatable transport member 222 may comprise a winding device 223.1; 223.2 for winding up a preparation in its elongated condition to form a wound condition. The winding device has two rotatable axles 223.1; 223.2, which are configured to be electrically driven and controlled by an electronic control device 280 of the production machine. The two rotatable axles are arranged at positions offset form the rotation axis R1 of the rotatable transport member 222. The rotatable transport member 222 and/or the winding device are configured to wind up a preparation 212 in its elongated condition in the mounting position at 243.3, in particular if the rotatable axle 223.1 is positioned in front of the opening 16 and within the opening, such that the formation of the preparation 2 in its compact condition takes place in a compacting position shown in FIGS. 9a and 9b, which is located in front of the opening and even within the opening 16, —and thereby at least in part directly within the hollow space 14 of the first halve-capsule shell 11; 11'— when the first halve-capsule shell is in the mounting position at 243.3. Thereby, transferring of the preparation into the capsule is remarkably facilitated.

Figure 9B:
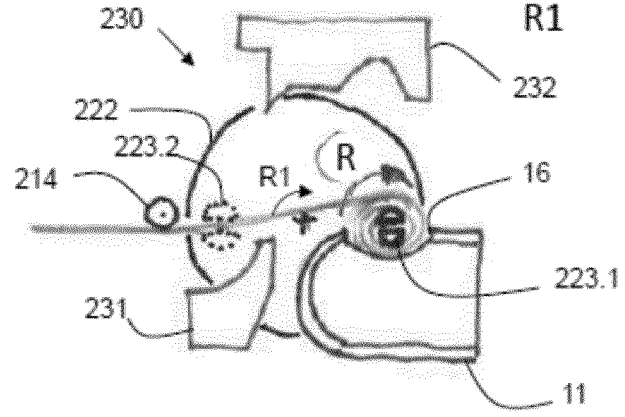
FIG. 9b exemplarily shows the equipment device of FIG. 9a, in a second step, wherein the elongated preparation is readily wound up and is now cut by a cutting device.

FIG. 9b exemplarily shows the equipment device 201 of FIG. 9a, in a second step, wherein the elongated preparation 212 is readily wound up and is now cut by a cutting device 230.

The production machine comprises a cutting device 230 for cutting the preparation to form the preparation, which is to be inserted into the hollow space of the first halve-capsule shell. The cutting device comprises a first part 231, having a first cutting edge, and a second part 232, having a second cutting edge.

Figure 9C:
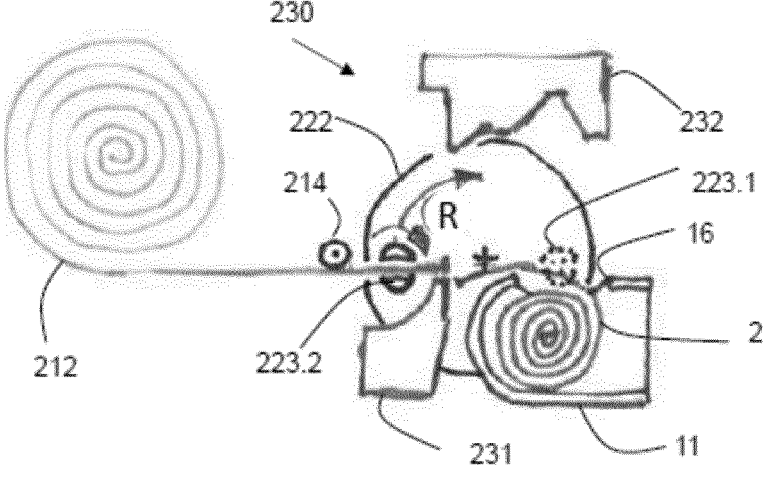
FIG. 9c exemplarily shows the equipment device of FIG. 9b, in a third step, wherein the elongated preparation is readily wound up, cut from the storage roll and was inserted into the hollow space of the first halve-capsule shell through the opening, by actuation form an actuation device.

FIG. 9c exemplarily shows the equipment device 201 of FIG. 9b, in a third step, wherein the elongated preparation 2 is readily wound up, cut from the storage roll 212 and was inserted into the hollow space 14 of the first halve-capsule shell 11 through the opening 16, by actuation form an actuation device 233, which is a part of the second part 232, in the present case. The production machine comprises an actuation device 233 for moving the preparation 2 in its compact condition from the compacting position to its end position inside the hollow space 14 of the first halve-capsule shell 11.

Figure 10A:
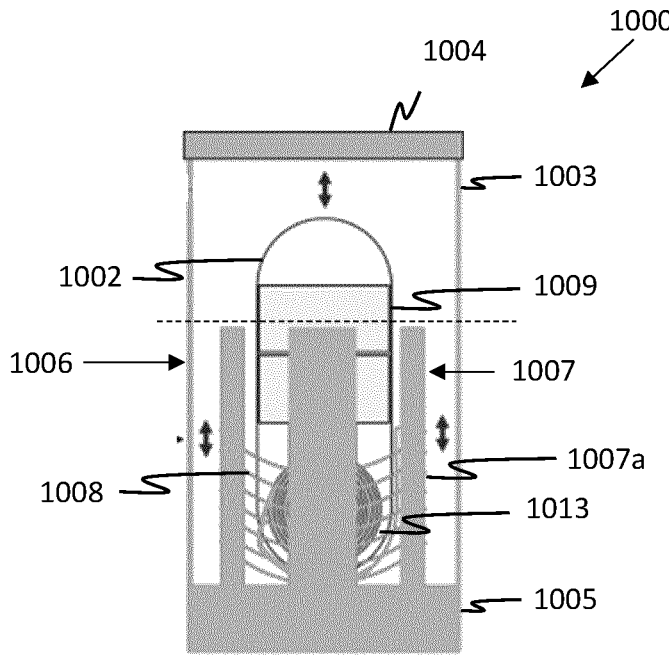
FIG. 10a shows a schematic cross section of an applicator with a pharmaceutical dosage form arranged inside the bottom part of the applicator holder and which is covered by an applicator cap.

FIG. 10a shows a schematic cross section of an applicator 1000 with a pharmaceutical dosage form 1002 having a preparation 1013 arranged inside the bottom part 1005 of the applicator holder 1007 and which is covered by an applicator cap 1003 comprising a lid 1004. The bottom part 1005 is indicated by a dotted line as to separate the bottom part from the top, i.e. the cap 1003, whereas both parts form the housing 1006 of the applicator 1000. The dosage form 1002 is positioned inside the housing 1006, in detail, inside in the holder 1007. The dosage form 1002 is therefore vertically, i.e. along an axis indicating its elongated shape, arranged inside the holder 1007. The holder 1007 comprises bars 1007a. The bars running along the dosage form 1002 and serve to support the dosage form 1002, i.e. the capsule device in its vertical position inside the holder structure 1007. A retainer 1008 is wrapped around the bars 1007a. Further contained in the dosage form 1002 are sinker elements 1009. The bar structure of the holder 1007 allows the dosage from 1002 to move in the vertical direction as indicated by arrows.

Figure 10B:
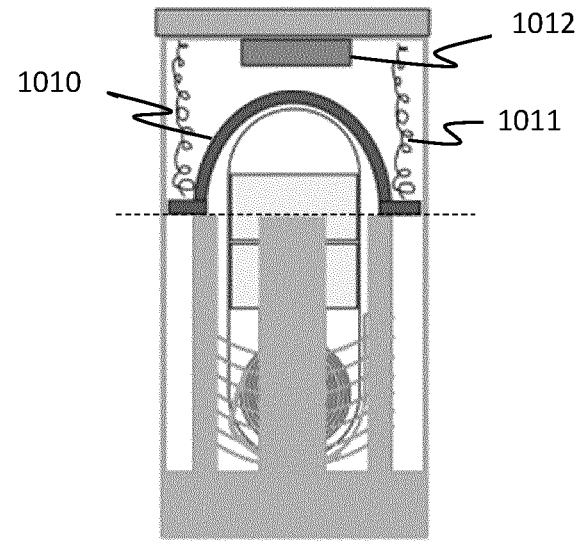
FIG. 10b shows a schematic cross section of an applicator with a pharmaceutical dosage form arranged inside and with an improved applicator cap.

FIG. 10*b* shows a schematic cross section of the applicator as shown in FIG. 10*a*. To suppress vertical movement of the dosage from 1002, in case the applicator 1000 is turned upside down or is shaken, a curved holder 1010 is positioned on the spherically shaped cap of the dosage form 1002. The holder 1010 therefore preferably has the similar outer contour as the end cap of the dosage form 1002. Further, the holder 1010 is fixed by springs 1011, which also press the holder 1010 onto the cap of the dosage form 1002. Therefore, the dosage form 1002 cannot move in the vertical direction. Further, the lid 1004 of the applicator 1000 comprises a dry agent 1012 to prevent the dosage form 1002 from becoming unusable.

FIG. 11 illustrates a semitransparent view of the pharmaceutical dosage form 1100. The dosage form 1100 comprises a first halve-capsule shell 1102 and a second halve-capsule shell 1101 telescoped into each other. The aperture 1106 is obtained by sliding the first 1102 and second 1101 halves over each other such that the opening 1104 of the first halve 1102 is partially covered to form the aperture 1106. The preparation 1105 is shown in the compact form, whereas the end of the preparation 1107 extends out of the aperture 1106 into the outside of the dosage form 1100. The dosage form 1100 further comprises sinker elements 1103 which are drawn on top of the preparation 1105. The sinker elements 1103 are fixed to prevent vertical movement of the elements 1103 in the length axis of the dosage form 1100 by a notch 1108. Preferably a plurality of notches 1108 are distributed within the wall of the dosage form 1100.

LIST OF REFERENCE SYMBOLS

FIGS. 1*a*-1*c*
1 pharmaceutical dosage form
2 preparation
2*a* end part of the preparation
3 capsule device
3*a* first halve-capsule shell
3*b* second halve-capsule shell
4 hollow space
5 aperture
5*a*, 5*a'* surface of the capsule wall
6 opening of the first halve-capsule shell
7 portion of end part of preparation
FIGS. 2*a*-2*e*, 3*a*-3*e*, 4*a*-4*d*
10 pharmaceutical dosage form
11 first halve-capsule shell
11*a* spheroid cap
11*b* hollow-cylindrical wall
11*c* wall of capsule
12 second halve-capsule shell
12*a* spheroid cap
12*b* hollow-cylindrical wall
12*c* area of wall of capsule
13 capsule device
14 hollow space
15 aperture
16 opening
17 hollow-cylindrical wall part
18 banderole
60 sinker element
FIG. 5*a*, 5*b*
901 drinking cup
902 applicator
903 capsule device
904 retainer
905 preparation FIGS. 6*a*-6*e*
100 Machine
101 retainer
101*a* retainer end part
102 holder of the applicator
105*a* first halve-capsule shell
105*b* second halve-capsule shell
106 clamping jaws
107 guiding means
108 cutter
109 support clutch
110 cutting unit
111 housing of the applicator
112 axis
113 bonding area
114 support
115 sinker elements
116 gripping element
117 end cap
FIG. 7
701 preparation
702 retainer
FIGS. 8, 9*a*-9*c*
200 production machine
201 equipment device
210 storage device
211 axis
212 storage roll of preparation
212*a* end part of the preparation
213 guiding unit
214 roll
220 transport device
222 rotating disk
223.1 compacting device
223.2 compacting device
230 cutting device
231 first part of cutting device
232 second part of cutting device with cutting edge
233 actuation device
240 positioning device
241 rotatable platform
242 axis
243.1 holding members
243.2 holding members
243.3 holding members
243.4 holding members
251 feeding device
251 devices
252 devices
260 connecting device
261 movable element
270 reception station
280 control device
FIG. 10*a*, 10*b*
1000 applicator
1002 pharmaceutical dosage form
1003 applicator cap
1004 lid
1005 bottom part of applicator
1006 housing
1007 holder
1008 retainer
1009 sinker elements
1010 curved holder
1011 springs
1012 dry agent
1013 preparation

FIG. 11

1100 pharmaceutical dosage form
1101 second halve-capsule shell
1102 first halve-capsule shell
1103 sinker elements
1104 opening
1105 preparation
1106 aperture
1107 end part of the preparation
1108 notch

The invention claimed is:

1. A capsule device for the application to a mucous membrane, configured to accommodate a pharmaceutical preparation having an elongated shape and comprising an active pharmaceutical ingredient, and capable of being arranged in a compact condition and in an expanded condition, the capsule device comprising a hollow space for accommodating the preparation in the compact condition, the capsule device having an aperture, configured to allow a first end of the preparation in the compact condition to extend through the aperture such that the preparation can be transferred from its compact condition in the hollow space to its expanded condition in the surrounding area of the capsule device, the capsule device comprising a first halve-capsule shell and a second halve-capsule shell, which are joined by overlapping the first halve-capsule shell and the second halve-capsule shell in a joined position, characterized in that the first halve-capsule shell has a hollow-cylindrical wall including an opening, and the second halve-capsule shell has a wall overlapping a cross-section of the opening thereby forming the aperture of the capsule device in the joined position.

2. The capsule device according to claim 1, wherein the hollow-cylindrical wall of the first halve-capsule shell is closed at a first end and open at a second end, and wherein the opening is fully surrounded by the material of the hollow-cylindrical wall.

3. The capsule device according to claim 1, wherein the hollow-cylindrical wall of the first halve-capsule shell is closed at a first end and open at a second end, and wherein the opening is formed as a recess starting at the second end and extending towards the first end.

4. The capsule device according to claim 1, wherein the cross-section of the opening is dimensioned to receive the preparation in its compact condition before joining the first halve-capsule shell and the second halve-capsule shell, wherein in the joined position, the aperture defined by the opening and a wall of the second halve-capsule shell has a cross-section dimensioned to prevent the preparation in its compact condition from passing through the aperture.

5. The capsule device according to claim 1, wherein the size A_o of the cross-section of the aperture is a fraction f of the size A_a of the cross-section of the opening, wherein $A\_o = f * A\_a$.

6. The capsule device according to claim 5, wherein $0.0010 < f < 0.7500$.

7. The capsule device according to claim 1, wherein, in the joined position, the first halve-capsule shell is inserted into the second halve-capsule shell.

8. The capsule device according to claim 1, wherein the aperture is a slit-like opening, configured for allowing the preparation to pass through the aperture, the cross-section (CS) of the aperture being larger than the cross section of the strip-like preparation, when the latter is extending through the aperture.

9. The capsule device according to claim 1, wherein the capsule device is configured to be suitable to be swallowed by a patient.

10. The capsule device according to claim 1, which comprises a sinker device, which occupies a part of the hollow space and which provides an additional weight to the capsule device.

11. A method of producing a capsule device as defined in claim 1 for accommodating a pharmaceutical preparation, comprising the steps of:

a) Providing the first halve-capsule shell having a hollow-cylindrical wall including an opening and the second halve-capsule shell;

b) Sliding the second halve-capsule shell and the first halve-capsule shell to a joined position, wherein the wall of the second halve-capsule shell overlaps a cross-section of the opening of the first halve-capsule shell, thereby forming the aperture of the capsule device in the joined position.

12. The method of claim 11, wherein step a) comprises the further steps:

a) Providing a material for forming the capsule device, the first and second halve-capsule shell;

b) Generating an opening, in particular a rectangular opening, in the material of the first and/or the second halve-capsule shell.

13. The method of claim 12, wherein the opening is generated in the formed hollow-cylindrical wall material of the first and/or second halve-capsule shell.

14. A pharmaceutical dosage form, comprising the capsule device according to claim 1 and a pharmaceutical preparation having an elongated shape and comprising an active pharmaceutical ingredient, and capable of being arranged in a compact condition and in an expanded condition.

15. A method of producing a pharmaceutical dosage form according to claim 14, the method comprising the following steps:

a) Providing the preparation having an elongated shape and comprising an active pharmaceutical ingredient;

b) Providing the first halve-capsule shell having a hollow-cylindrical wall including an opening and the second halve-capsule shell;

c) Accommodating the preparation, in a compact condition, through the opening into the first halve-capsule shell, such that a part or an end of the preparation extends through the opening;

d) Sliding the second halve-capsule shell over the first halve-capsule shell or sliding the first halve-capsule shell over the second halve-capsule shell to the joined position, thereby reducing the cross-section of the opening, while the end of the preparation extends through the opening, until the opening forms the aperture of the capsule device in the joined position of the first and second halve-capsule shells.

16. The method of claim 15, comprising the following step:

after step a) or b) providing a rotation axle (X), and winding the preparation in its elongated condition by rotating the rotation axle, until the preparation has reached a compact condition.

17. The method of claim 16, further comprising the following step:

after step a) or b) providing a rotation axle (X), and, positioning the same in front of the opening or within the cross-section of the opening.

18. The method of claim 17, further comprising winding the preparation in its elongated condition by rotating the rotation axle, thereby using the opening for guiding and/or aligning the preparation, until the preparation has reached a compact condition.

19. The method of claim 15, comprising the following step:

after step b) or c) positioning a sinker device within at least a part of the hollow space of the first and/or the second halve-capsule shell.

20. A kit comprising a pharmaceutical dosage form according to claim 14, a drinking cup, and an applicator for administering the pharmaceutical dosage form to a patient, wherein the applicator is in fluid connection with the drinking cup and comprises the pharmaceutical dosage form and wherein the preparation of the pharmaceutical dosage form is connected to the applicator by a retainer for withdrawing the preparation from the capsule device after administration to the patient.

* * * * *